(12) United States Patent
Petyaev

(10) Patent No.: US 7,419,657 B2
(45) Date of Patent: Sep. 2, 2008

(54) TREATMENT OF ATHEROSCLEROTIC DISORDERS

(75) Inventor: Ivan Petyaev, Cambridge (GB)

(73) Assignee: Cambridge Theranostics Ltd., Cambridge (GB)

( * ) Notice: Subject to any disclaimer, the term of this patent is extended or adjusted under 35 U.S.C. 154(b) by 633 days.

(21) Appl. No.: 10/225,460

(22) Filed: Aug. 22, 2002

(65) Prior Publication Data

US 2003/0190315 A1     Oct. 9, 2003

Related U.S. Application Data

(60) Provisional application No. 60/355,655, filed on Feb. 6, 2002, provisional application No. 60/323,127, filed on Sep. 18, 2001.

(30) Foreign Application Priority Data

| Aug. 22, 2001 | (GB) | .................. | 0120428.8 |
| Feb. 6, 2002 | (GB) | .................. | 0202774.6 |
| Feb. 27, 2002 | (GB) | .................. | 0204611.8 |
| Jul. 16, 2002 | (GB) | .................. | 0216530.6 |
| Jul. 18, 2002 | (GB) | .................. | 0216755.9 |

(51) Int. Cl.

| A61K 31/74 | (2006.01) |
| A61K 31/665 | (2006.01) |
| G01N 33/53 | (2006.01) |
| G01N 33/561 | (2006.01) |
| C12Q 1/28 | (2006.01) |
| C07K 16/00 | (2006.01) |
| C07H 17/08 | (2006.01) |
| C07G 11/00 | (2006.01) |

(52) U.S. Cl. .................. 424/78.05; 424/78.07; 435/7.2; 435/7.32; 435/28; 514/68; 514/100

(58) Field of Classification Search ........................ None
See application file for complete search history.

(56) References Cited

U.S. PATENT DOCUMENTS

| 5,278,189 A | 1/1994 | Rath et al. |
| 6,281,199 B1 | 8/2001 | Gupta |
| 2004/0116350 A1 | 6/2004 | Wentworth et al. |
| 2005/0129680 A1 | 6/2005 | Wentworth et al. |

FOREIGN PATENT DOCUMENTS

| EP | 0561744 A1 | 9/1993 |
| EP | 0669132 A1 | 8/1995 |
| WO | WO 92/05780 A1 | 4/1992 |
| WO | WO 97/41227 | 11/1997 |
| WO | WO 98/57622 A1 | 12/1998 |
| WO | WO 01/22958 A2 | 4/2001 |
| WO | WO 02/22573 | 3/2002 |

OTHER PUBLICATIONS

Gupta et al. JACC. Feb. 1997, vol. 29, p. 209A, abstract 755-2.*
Shoenfeld et al. Trends in Immunology. Jun. 2001, vol. 22, No. 6, pp. 293-295.*
Gupta et al. Circulation. 1997, vol. 96, No. 2, pp. 404-407.*
Nevinsky et al. Biochemistry. 2000, vol. 65, No. 11, pp. 1245-1255.*
Wikipedia. 2006, en.wikipedia.org/wiki/Chlamydia_pneumoniae, 4 pages.*
Henry, J. B. Clinical Diagnosis and Management by Laboratory Methods. 1979, vol. II, 16$^{th}$ Edition, W.B. Saunders Co., Philadelphia, London, Toronto, pp. 1483-1486.*
Science Lab.com. www.scienclab.com/XMSDS-Picolinic_acid-9926555, May 2007.*
Vertuani et al (Curr. Pharm. Design, Oct. 2004: 1677-1694).*
Kalayoglu et al, Cellular Oxidation of Low-Density Lipoprotein by *Chlamydia pneumoniae*, J Infect Disease, 1999, vol. 180, pp. 780-790.
Burian et al, Independent and Joint Effects of Antibodies to Human Heat-Shock Protein 60 and *Chlamydia pneumoniae* Infection in the Development of Coronary Atherosclerosis, Circulation, 2001, vol. 103, pp. 1503-1508.
Petyaev et al, Superoxide Dismutase Activity of Antibodies Purified from the Human Arteries and Atherosclerotic Lesions, Biochemical Society Transactions, Feb. 1998, vol. 26, No. 1, p. S43.
Sobal et al, Influence of Acetylsalicylic Acid on Oxidation of Native and Glycated Low-Density Lipoprotein, Life Sciences, Apr. 7, 2000, vol. 66, No. 20, pp. 1987-1998.
Steer et al, Aspirin protects low density lipoprotein from oxidative modification, Heart, 1997, vol. 77 No. 4, pp. 333-337.
Gurfinkel et al, Emerging role of antibiotics in atherosclerosis, American Heart Journal, Nov. 1999, vol. 138, No. 5, pp. S537-538.
Schwenke et al, Vitamin E Combined With Selenium Inhibits Atherosclerosis in Hypercholesterolemic Rabbits Independently of Effects on Plasma Cholesterol Concentrations, Circ. Res., Aug. 24, 1998, vol. 83, pp. 366-377.
Fong et al, Can an Antibiotic (Macrolide) Prevent *Chlamydia pneumoniae*-Induced Atherosclerosis in a Rabbit Model? Clinical and Diagnostic Laboratory Immunology, Nov. 1999, vol. 6. No. 6, pp. 891-894.
Muhlestein et al, Infection With *Chlamydia pneumoniae* Accelerates the Development of Atherosclerosis and Treatment With Azithromycin Prevents It in a Rabbit Model, Circulation, vol. 97, pp. 633-636, 1998.
Petyaev, Extraction of anti-lipoprotein abzymes from human atherosclerotic lesion: antibodies which bind and oxidise LDL, J Submicroscop Cytol Pathol; vol. 32, pp. 477 (2000).
Wentworth et al, "Antibodies have the intrinsic capacity to destroy antigens", PNAS, Sep. 26, 2000, vol. 97, No. 20, pp. 10930-10935.

* cited by examiner

*Primary Examiner*—G. R. Ewoldt
*Assistant Examiner*—DiBrino Marianne
(74) *Attorney, Agent, or Firm*—Nixon & Vanderhye P.C.

(57) ABSTRACT

The present invention relates to the identification of lipid oxidizing abzymes as a key pathogenic factor in atherosclerotic disorders. Methods and means for the reduction of abzyme mediated lipid oxidation in the vascular system are provided as therapeutic approaches for the treatment of atherosclerotic disorders. Methods are provide for determining the efficacy of treatment.

3 Claims, 14 Drawing Sheets

Interaction of ovine Chlamydia with anti-ApoB antibodies

Legend:
- ○ Chlamydia + Anti-ApoB antibodies
- □ [Anti-ApoB antibodies + ApoB] + Chlamydia X-axis: Ovine Chlamydia, in $10^6$ cells/ml
Y-axis: Absorption at 340nm

Figure 13

TREATMENT OF ATHEROSCLEROTIC DISORDERS

The present application claims benefit of U.S. Provisional application Nos. 60/323,127 and 60/355,655, filed Sep. 18, 2001 and Feb. 6, 2002, respectively, as well as GB application Nos. 0120428.8, 0202774.6, 0204611.8, 0216530.6 and 0216755.9, filed Aug. 22, 2001, Feb. 6, 2002, Feb. 27, 2002, Jul. 16, 2002 and Feb. 18, 2002, respectively.

FIELD OF INVENTION

The present invention relates to methods of treating atherosclerosis and related conditions in an individual.

BACKGROUND OF INVENTION

Auto-antibodies against such lipids as cholesterol [Swartz G. M., Jr., et al Proc. Natl. Acad. Sci. USA (1988), 85, 1902-1906, Alving C. R. and Swartz G. M., Jr. Critical Reviews in Immunology (1991), 10, 441-453.], phospholipids [Alving C. R. Biochem. Soc. . Trans. (1984), 12, 342-344.] and low density lipoproteins (LDL) are found in human plasma [Kabakov A. E. et al Clin. Immun. Immunopath. (1992), 63, 214-220, Mironova M et al Ibid. (1997), 85, 73-82.] and are involved in the development of atherosclerosis [Lopes-Virella M. F. and Virella G. Clin. Immun. Immunopath. (1994), 73, 155-167, Kiener P. A. et al Arterioscler. Thromb. Vasc. Biol. (1995), 15, 990-999.].

Separately, neither antibodies nor LDL are a pathogenic factor, only the immune complex of the two [Tertov V. V et al Atherosclerosis (1990), 81, 183-189, Orekhov A. N. et al Biochem. Biophys. Res. Comm. (1989), 162, 206-211.].

Immune complexes comprising unmodified plasma lipoproteins are known to have a low atherogenicity. However, if the lipoproteins become modified, in particular oxidised, these immune complexes become highly atherogenic [Orekhov A. N. et al Biobhem. Biophys. Res. Comm. (1989), 162, 206-211, Orekhov A. N. et al Arterioscler. Thromb. Vasc. Biol. (1991), 11, 316-326.]. Oxidation of plasma lipids, which takes the form of peroxidation, is generally considered to be responsible for the development of atherosclerosis and is a consistently observed and published feature of this disease in the clinic [Goto Y. In: Lipid Peroxides in Biology and Medicine, Ed. Yagi K., Academic Press, New York, London, Tokyo (1982), 295-303, Halliwell B. and J. M. C. Gutteridge, Free Radicals in Biology and Medicine, Clarendon Press, Oxford, 1989, Schultz D et al Arterioscler. Thromb. Vasc. Biol. (2000), 20, 1412-1413.]. However, until the present disclosure, the cause of this peroxidation in plasma was obscure.

SUMMARY OF INVENTION

The present invention relates to the discovery that a particular sub-group of auto-antibodies are capable of both binding and oxidising lipids and lipoproteins. These catalytic antibodies ('abzymes') react with and oxidise low density lipoprotein to generate atherogenic factors and are the first reported example of anti-lipid abzymes.

In various aspects, the present invention relates to the use of lipid oxidising antibodies as a therapeutic target in methods of treating atherosclerotic disorders.

An aspect of the invention provides a method of treating of an individual having an atherosclerotic disorder which comprises reducing antibody mediated lipid peroxidation activity in the vascular system of said individual.

BRIEF DESCRIPTION OF THE FIGURES

FIG. 13 shows the cross-reaction of anti-apolipoprotein B antibodies with Chlamydia.

DETAILED DESCRIPTION OF INVENTION

Figure 1:
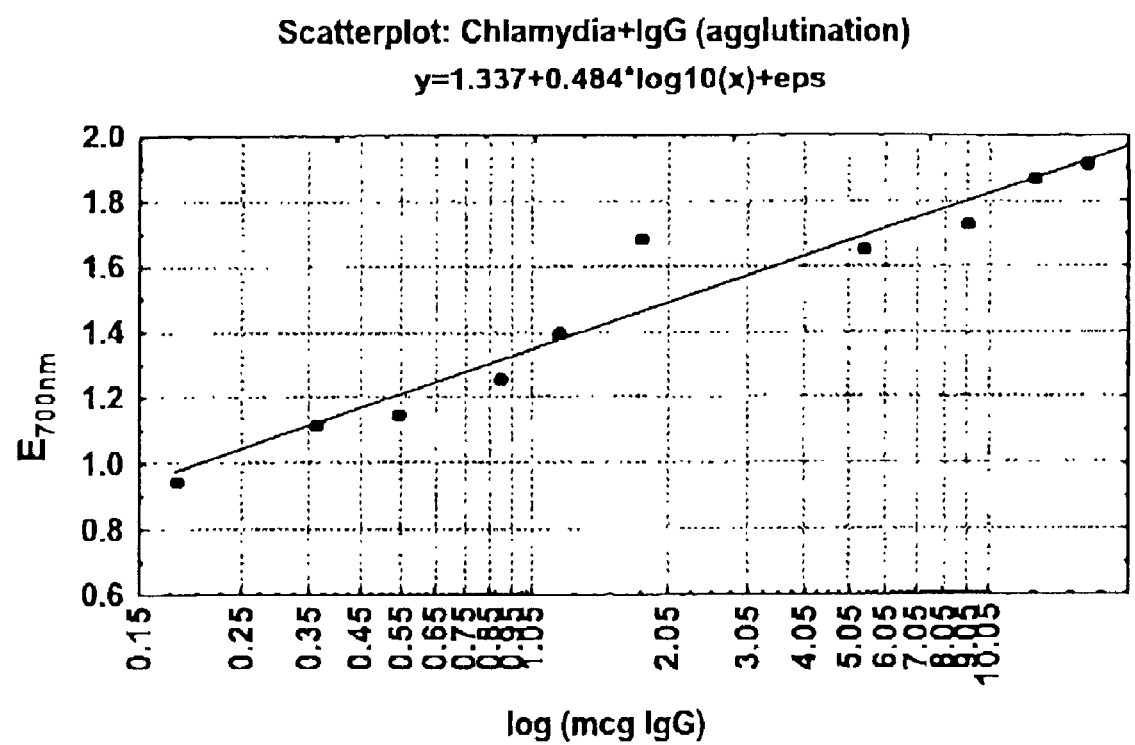
FIG. 1 shows the results of an agglutination reaction between 100 μl of ovine Chlamydia and IgG extracted from human atherosclerotic lesion.

As described above, the present invention, in various aspects, relates to the use of lipid oxidising antibodies as a therapeutic target in methods of treatment of atherosclerotic disorders.

A method of treatment of an individual having an atherosclerotic disorder may comprise reducing antibody mediated lipid oxidation activity in the vascular system of said individual.

Antibody mediated lipid oxidation activity may be reduced by administering an inhibitor of a lipid oxidising antibody to said individual or by reducing the amount or level of lipid oxidising antibody in the vascular system of the individual as further described below.

A lipid oxidising antibody is a molecule which is a member of the immunoglobulin super-family that is associated with both binding and catalytic activity. After purification, for example, using protein G, a lipid oxidising antibody displays both binding to antigen and catalytic activity (i.e. lipid oxidation).

Both binding and catalytic activities may be intrinsic to a lipid oxidising antibody. Alternatively, the lipid oxidising activity may be due to a catalytic molecule which is tightly bound to the antibody and co-purifies with it (for example, using a Protein G/Protein A or Protein L column) in a complex. This catalytic molecule may be an immunoglobulin or a non-immunoglobulin, such as an enzyme or a metal ion. After purification, the complex displays binding activity from the antibody and catalytic activity from the catalytic molecule. A lipid oxidising antibody may, alternatively, initiate lipid oxidation by another mechanism e.g. by altering the lipid antigen environment (e.g. via the activation of monocytes) or altering the lipid or lipoprotein to facilitate oxidation of lipid.

A catalytic antibody may be specific for a particular epitope which is carried by a number of antigens and may therefore bind to different antigens which carrying the same epitope. The antibody may show no significant binding to other epitopes. The antibody is thus said to 'bind specifically' to the epitope or to an antigen comprising the epitope. An epitope which is recognized by the antibody may be shared by a host molecule and an antigen from an infectious agent, for example a bacterium, fungus, virus or protozoa. A lipid oxidising antibody produced by a host in response to a foreign antigen, for example during pathogenic infection, may thus cross-react with host lipids or lipoproteins or other antigens.

The lipid oxidising antibody may thus bind to both a host molecule and a foreign antigen and may catalyze the oxidation of one or both of these molecules. An antibody molecule may oxidise, in particular peroxidise, the lipid portion of plasma lipoproteins, in particular low density lipoproteins.

An antigen which is bound by a lipid oxidising antibody may be a member of a family of molecules sharing high sequence identity (i.e. homologues) which are found in a range of infectious agents (for example, in two or more species of gram –ve bacteria) or the antigen may be specific to a particular infectious agent (ie. it does not have homologues in other species). Moreover, the same epitope may be present in antigens from different infectious agents which do not otherwise share high levels of sequence identity (i.e. non-homologues). Examples of antigens which are common to a range of infectious agents include apo-lipoprotein B, OmpA, lipopolysaccaride, hsp60 MQMP, (P)OMP, p54 and lipid A.

Antibody molecules which catalyze the oxidation of lipid are referred to herein as catalytic antibody molecules, anti-lipid abzymes, abzymes or lipid oxidising antibodies. As described above, such catalytic antibodies may have an intrinsic or inherent lipid oxidase activity or other activity which leads to lipid oxidation or may be naturally associated (i.e. bound or attached in a non-covalent manner in their natural state within the body) with a molecule having lipid oxidase activity.

An atherosclerotic disorder suitable for treatment by the methods described herein may include atherosclerosis, ischaemic (coronary) heart disease: myocardial ischaemia (angina), myocardial infarction; aneurismal disease; atheromatous peripheral vascular disease: aortoiliac disease, chronic and critical lower limb ischaemia, visceral ischaemia, renal artery disease, cerebrovascular disease, stroke, atherosclerotic retinopathy and hypertension. Such conditions may be medical or veterinary conditions.

Individuals which may be the subject of methods of the present invention include humans and non-human animals, including domestic animals such as dogs, cats, horses and parrots, farm animals such as sheep and cattle and rare or exotic animals such as elephants and tigers. References to 'human' herein should be understood to include 'non-human animal' except where the specific context dictates otherwise.

The reduction in peroxidation may be preceding by the step of assessing the individual for an atherosclerotic disorder. This may be achieved by determining the antibody mediated lipid oxidation activity of a sample obtained from the individual as described below.

A method may thus comprise testing the ability of an antibody from a sample obtained from an individual to oxidise lipid, and; reducing antibody-mediated lipid oxidising activity in the vascular system of the individual.

An individual who is identified as having lipid oxidising antibodies indicative of an atherosclerotic condition may be subjected to therapeutic treatment according to the present methods to alleviate the condition or its symptoms. The level or amount of lipid-oxidising abzymes is indicative of the severity of the condition and may be used to determine the particular treatment regime, as described herein.

A method may further comprise determining the antibody mediated lipid oxidation activity of a sample obtained from the individual following said reduction in antibody mediated lipid oxidation activity.

Antibody mediated lipid oxidation activity may be determined as described below.

The experimental data in the present application further shows that a sub-group of the antibodies which are raised in response to Chlamydia infection are auto-antibodies which cross react with host antigen and are responsible for plasma lipid peroxidation. Catalytic anti-Chlamydia antibodies are shown to be present in anti-lipoprotein IgG fractions extracted from human atherosclerotic lesions and the sera of patients with clinical complications of atherosclerosis, but absent from IgG extracted from the sera of healthy people. Catalytic antibodies which bind and oxidise lipid as described herein may therefore be reactive with i.e. bind to, a Chlamydia cell.

Whilst atherosclerosis has been linked in the past to the presence in the arterial wall of the bacteria *Chlamydia pneumoniae* [Roivainen M. et al Circulation (2000), 101, 252-257, Siscovick D. S. et al J. Infect. Dis. (2000), 181, Suppl. 3, S417-420], a serological test to detect specific anti-Chlamydia antibodies in the plasma or serum of patients [Mendall M. et al (1995) J. Infect. 30 121-128, Wang S-P et al (1970) 70 367-374] cannot be used to identify or distinguish a patient with atherosclerosis. A significant part of the population have a history of Chlamydia infection and, as result of this, have specific anti-Chlamydia antibodies in their sera, without any clinical manifestation of atherosclerosis [Davidson M. et al Circulation (1998), 98, 628-633m, Song Y. G. et al Yonsei Med. J.(2000), 41, 319-327. ]. The presence of anti-Chlamydia antibodies per se in the plasma or serum is not therefore indicative of atherosclerosis.

However, catalytic anti-Chlamydia antibodies which cross-react with human antigens and catalyse the oxidation of plasma lipoproteins are shown herein to be useful as targets for the treatment of atherosclerotic disorders.

A lipid oxidising antibody may thus bind or be reactive with a Chlamydia cell antigen i.e. the antibody molecules may be anti-Chlamydia abzymes or antibody molecules.

A Chlamydia antigen as described herein may be any immunogen or immunogenic component of a Chlamydia cell i.e. a molecule from Chlamydia which evokes or is capable of evoking an immune response in a mammal against the Chlamydia cell, for example Hsp60 (Huittinen et al (2001) Eur Resp. J. 17(6) 1078-1082, Kinnunen A. et al (2001) Scand. J. Immunol. 54(1-2) 76-81). Preferably, the antigen is a protein or lipid antigen i.e. it comprises or consists of a lipid group or moiety. A lipid antigen may be, for example, a lipid, lipoprotein or other lipid associated cell component which binds anti-Chlamydia antibodies and the term 'lipid antigen' refers to any of these components. Such an antigen may be purified and/or isolated or comprised within a Chlamydia cell. Suitable methods for purifying and/or isolating such a lipoprotein are well known in the art, for example HPLC.

Antibodies raised against human apo-lipoprotein B have been shown to be reactive with Chlamydial cells (see Example 7). In some embodiments, a lipid oxidising antibody as described herein may thus be reactive with human apolipoprotein B. A Chlamydial cell may be a cell from a species belonging to the *Chlamydia psittaci* group. The *Chlamydia psittaci* group includes *Chlamydia psittaci* and *Chlamydia pneumoniae*. In some preferred embodiments, the Chlamydial cell is an ovine *Chlamydia psittaci* cell. Suitable preparations of live ovine *Chlamydia psittaci* in a lyophilised form are available commercially (Intervet).

An inhibitor of a lipid oxidising antibody may inhibit the binding of a lipid oxidising antibody to a lipid antigen (i.e. block the binding site of the abzyme) or may inhibit the lipid oxidising activity of the antibody (i.e. block the catalytically active centers).

Inhibitors which block the catalytically active centres of the abzymes may include metal chelators, examples of which are shown in Table 7. Metal ions of transient valence at the catalytic centre of an abzyme are specifically targeted by such chelators to neutralise the catalytic properties of the abzyme. Metal chelators which inhibit abzymes include aspirin.

Other such inhibitors include substrate antagonists which prevent binding of the abzyme with its target epitope(s) in the organism of the host. Binding antagonists may be either be peptide, lipid, polysaccharide, or any other synthetic or naturally occurring product which imitates an epitope of the abzyme. Such an antagonist may be modeled on a lipid antigen, which may for example be a host, i.e. a human antigen or a pathogen antigen.

The active centre of an abzyme may be modified in other ways to inactivate its catalytic properties. For example, the active centre of an abzyme may contain a photo-(UV-)sensitive group(s) which may be modified by an extra-corporal (UV)irradiation of plasma/serum to inactivate the lipid peroxidation properties of these molecules.

Examples of inhibitors which block the binding sites of the abzymes include anti-idiotypic antibody molecules, including Fab/Fv or other antibody fragments and derivatives, or peptide molecules presenting the fragment(s) of the complementary loop of their active centres (i.e. which imitate the anti-idiotypic antibody molecule) which would enable them to inhibit the binding of the abzymes with their target antigens. Suitable antibody molecules may be made by using a polyclonal or monoclonal strategy or by phage display.

Other compounds with antagonistic properties may be used to compete with antigen for the binding site of an abzyme for example, a peptide, lipid, polysaccharide, or any other synthetic or naturally occurring product which mimics an epitope to which the abzyme binds. Other compounds or chemical and physical procedures with can modify binding sites of the abzymes may also be used to disrupt binding, for example, irradiation as described above.

The data provided herein indicates that the anti-bacterial drug azithromycin is an inhibitor of abzyme activity. Thus, candidate inhibitors may include both molecules structurally related to azithromycin and anti-microbial agents such as erythromycin, roxithromycin, ofloxacin, clinafloxacin, ciprofloxacin, clindamycin, azithromycin, doxycycline, minocycline and tetracycline.

Aspects of the invention provide methods of treatment of atherosclerosis comprising administration of azithromycin to an individual and methods of treatment comprising administration of azithromycin in combination with a second abzyme inhibitor, for example a metal chelator agent such as aspirin. For example, azithromycin and a chelator such as aspirin may be combined in a single composition or administered simultaneously or sequentially.

Aspects of the invention also provide the use of azithromycin in a method of inhibiting a lipid oxidising antibody, as described herein and a method of inhibiting a lipid oxidising antibody comprising contacting said antibody with an azithromycin molecule.

Antibody-mediated lipid peroxidation activity in the vascular system of an individual may be reduced by reducing the amount or level of lipid oxidising antibody in the vascular system of the individual.

A method of treatment of an atherosclerotic disorder may comprise eliminating or removing antibodies which oxidise lipid from the vascular system of a individual in need thereof.

Such a method may comprise the step of determining the presence or amount of lipid oxidising antibodies as described herein in a sample obtained from the individual before and/or after the elimination or removal step.

Antibodies which oxidise lipid i.e. (abzymes) may be removed from the vascular system i.e. from circulation in any one of a number of ways. The cells responsible for abzyme production may be inhibited, neutralized or eliminated, for example, using specific antibodies against this sub-population of B cells. Inhibition of abzyme production may be achieved either through the binding of the antibody or through the action of cytotoxic agents loaded onto these antibodies and delivered to the B cell.

The production of specific anti-abzyme anti-idiotypic antibodies may be activated. This may be achieved for example, by identifying suitable anti-idiotypic antibodies using phage display antibody techniques and introducing these antibodies or their encoding nucleic acid into the individual or by implantation of recombinant host cells which produce the anti-idiotypic antibodies.

Chemical, physical or biological systems may be implanted into the host which, either autonomously or in cooperation with host homeostasis/metabolism, would directly or non-directly inactivate, or neutralise, or eliminate circulating abzymes. For example, a polymer or other substance may be employed which carries high affinity epitope-imitating targets and is therefore capable of binding circulatory abzymes, but is also able to be absorbed and digested by phagocyte cells, thereby removing bound abzymes from circulation.

Patient plasma may be dialysed through sorbents or membranes to specifically remove abzymes from the circulation or plasma may be treated extra-corporeally by chemical or physical means to inactivate abzymes. The sorbent may, for example, be loaded with the specific epitope or the chelator to specifically remove abzymes from the circulation by using extracorporal dialysis systems. In other embodiments, serum or plasma may be irradiated extra-corporeally as described above to inactivate abzymes.

Specific anti-microbials, for example anti-Chlamydia bactericidal agents, may be used to remove lipid oxidizing antibodies from the vascular system by removing bacterial infection from the host. Such anti-microbials may also mobilise the body's own mechanisms of homeostasis to cease/block/eliminate the production of lipid oxidising antibodies. Examples of suitable anti-microbials are provided in Table 8.

A method may comprise a combination of one or more of the above approaches, which may be applied simultaneously or sequentially to an individual. For example, the lipid oxidation activity of the antibodies may be reduced or eliminated, for example using an inhibitor such as an anti-oxidant, whilst simultaneously or sequentially, the amount or level of lipid oxidizing antibodies in circulation is reduced, for example using an anti-microbial agent. Agents directed specifically against abzymes, such as anti-Chlamydia abzymes, may thus be used simultaneously or sequentially with anti-microbials to treat an atherosclerotic condition. The precise choice of agents, doses, duration and other parameters may be determined according to the individual case by a medical practitioner. This efficacy of a particular treatment may be determined for each individual case by monitoring changes in abzyme activity in the serum of the treated patients using methods described herein.

An aspect of the present invention provides a method of treating an individual having an atherosclerotic condition including;
  administering two or more agents selected from the group consisting of antioxidants, chelators and anti-microbial compounds to the individual.

A method of treatment of an atherosclerotic condition may include;
  administering two or more agents selected from the group consisting of antioxidants, chelators and anti-microbial compounds to the individual, and;
  determining the antibody-mediated lipid oxidation activity in the vascular system of said individual.

Suitable antioxidants, chelators and anti-microbial compounds are described elsewhere herein.

Another approach is the administration of a Chlamydia vaccine to reduce or eliminate abzyme activity (see Table 10—post vaccinated). Chlamydia vaccines may therefore be used to reduce or eliminate abzymes from the vascular system of humans and animals having atherosclerosis or to block abzyme production.

Further aspects of the present invention provide a chlamydia vaccine, in particular a *chlamydia pneumoniae* vaccine, for use in the treatment of an atherosclerotic disorder and a method of treatment of an atherosclerotic disorder comprising administering a chlamydia vaccine to an individual in need thereof.

A vaccine is a non-virulent material comprising one or more antigens from a pathogen, such as Chlamydia, in particular *chlamydia pneumoniae*, which stimulates active immunity in an individual and protects against infection by the pathogen or other closely related pathogens.

A chlamydia vaccine may be a non-virulent chlamydia cell, in particular a *chlamydia pneumoniae* cell, for example a heat-killed chlamydial cell or a component, extract or fraction of such a cell. Veterinary chlamydia vaccines are well-known in the art and formulations of live ovine *Chlamydia psittaci* in a lyophilised form are available commercially (Intervet).

A suitable Chlamydia vaccine, in particular a *Chlamydia pneumoniae* vaccine, may be in a medicinal (i.e. a non-veterinary) formulation. Such a formulation is suitable for administration to a human.

As described above, methods of the invention may comprise assessing an individual for an atherosclerotic disorder before, during and/or after treatment by determining the lipid oxidation activity of an antibody from a sample obtained from the individual. Lipid oxidation activity is indicative of an individual having an atherosclerotic condition and thus being a candidate for treatment in accordance with the present methods.

Lipid oxidation activity may be determined by testing the ability of an antibody from a sample obtained from the individual to oxidise lipid. For example, an antibody from a serum sample may be captured using an immobilised anti-idiotypic antibody, and the lipid oxidation activity of the captured antibody determined.

The lipid oxidising antibody may bind to a Chlamydia antigen. Binding to a Chlamydia antigen of an antibody molecule from a sample obtained from the individual which possesses lipid oxidation activity (i.e. oxidises lipids) or lipid oxidation of an antibody obtained from the individual which binds to Chlamydia antigen may be determined. Alternatively, both binding to a Chlamydia antigen and the lipid oxidation activity of an antibody molecule from a sample obtained from the individual may be determined.

A suitable sample may be a serum, plasma, blood or other biological sample, preferably a serum or plasma sample. An antibody or antibody molecule as described herein is preferably an IgG molecule.

The mode of determining binding is not a feature of the present invention and those skilled in the art are able to choose a suitable mode according to their preference and general knowledge.

Lipid oxidation activity, including lipid peroxidation activity, may be determined by determining the oxidation of host lipid (i.e. lipid from the sample), lipid from a foreign antigen such as a Chlamydia cell, or lipid from another source, which may for example be added as part of a testing method.

Lipid oxidation may be determined by measuring the accumulation of products or by-products, such as co-oxidised coupled reporter molecules or the disappearance or consumption of substrates such as non-modified lipids or co-substrates such as oxygen.

Many methods for determining lipid peroxidation are known in the art and are suitable for use in accordance with the present invention The precise mode of determining lipid oxidation is not a feature of the present invention and those skilled in the art are able to choose a suitable mode according to their preference and general knowledge.

Suitable methods are, for example, described in CRC Handbook of Methods for Oxygen Radical Research, CRC Press, Boca Raton, Fla. (1985), Oxygen Radicals in Biological Systems. Methods in Enzymology, v. 186, Academic Press, London (1990); Oxygen Radicals in Biological Systems. Methods in Enzymology, v. 234, Academic Press, San Diego, New York, Boston, London (1994), and Free Radicals. A practical approach. IRL Press, Oxford, New York, Tokyo (1996)

In preferred embodiments, oxidation is determined by determining the production (i.e. the presence or amount) of a lipid oxidation product.

Oxidation products and/or intermediates of the lipids in which oxidation was initiated may be determined or oxidation products and/or intermediates may be determined of lipids in which oxidation is propagated.

A suitable lipid oxidation product may include aldehydes such as malondialdehyde (MDA), (lipid) peroxides, diene conjugates or hydrocarbon gases. Lipid oxidation products may be determined by any suitable method. For example, lipid peroxidation products may be determined using RPLC (Brown, R. K., and Kelly, F. J In: Free Radicals. A practical approach. IRL Press, Oxford, New York, Tokyo (1996), 119-131), UV spectroscopy (Kinter, M. Quantitative analysis of 4-hydroxy-2-nonenal. Ibid.,133-145), or gas chromatography-mass spectrometry (Morrow, J. D., and Roberts, L. J. $F_2$-Isoprostanes: prostaglandin-like products of lipid peroxidation. Ibid., 147-157).

The peroxidation of lipid may lead to an oxidation of proteins, carbohydrates, nucleic acids and other types of molecules. The products of such oxidation can also be used for indirect measurement of the activity of the abzymes. In addition, peroxidation may lead to changes in the properties of reporter molecules associated with propagating lipid oxidation. As described below, reporter molecules may be encapsulated in these lipids, for example as liposomes, and release of the reporter molecule from the liposome is indicative of oxidation.

Suitable reporter substances and molecules may include intact luminous bacteria, luminol, lucigenin, pholasin and luciferin. Such substances may, for example, be coupled to $H_2O_2/O_2^{\bullet}/O_2$-utilizing molecules such as peroxidase, esterase, oxidase, luciferase, catalase, superoxide dismutase, perylene, $NAD^+$, and acridinium esters bis (trichlorophenyl) oxalate (Campbell A. K. Chemiluminescence. VCH, Ellis Horwood Ltd., England, 1988)

Other materials susceptible to free radical chain reactions may also be used to determine lipid oxidation. For example, lipid peroxidation, as a chain process, initiates and enhances the polymerization of acrylamide. Lipid oxidation may thus be determined by the determining the co-polymerisation of $^{14}C$-acrylamide (Kozlov Yu P. (1968) Role of Free Radicals in normal and pathological processes. Doctorate thesis—MGU Moscow 1968)

Since lipid and lipoprotein peroxidation is a free radical mediated process, lipid oxidising abzymes may be measured by detection of these radicals. Radicals may be detected or determined using intrinsic low-level chemiluminescence (with or without sensitisors)(Vladimirov, Y. A., and Archakov, A. I. Lipid Peroxidation in Biological Membranes. Nauka, Moscow (1972); Vladimirov, Y. A. Intrinsic low-level chemiluminescence. In: Free Radicals. A practical approach. IRL Press, Oxford, New York, Tokyo (1996), 65-82), electron spin resonance (with spin trapping (Mason, R. P. In vitro and in vivo detection of free radical metabolites with electron spin resonance. In: Free Radicals. A practical approach. IRL Press, Oxford, New York, Tokyo (1996), 11-24) or without spin trapping (Petyaev, M. M. Biophysical approaches in the diagnosis of cancer. Medicina, Moscow (1972)) or other techniques well known in the art. Lipid oxidation may also be determined by determining the consumption of fatty acids or other substrates of this reaction.

In some preferred embodiments, the production of malondialdehyde (MDA) is determined, following reaction with 2-thiobarbituric acid (conveniently 1 mM ) by measuring absorbance at an appropriate wavelength, for example 525 nm.

Lipid which is oxidised by an anti-Chlamydia abzyme may include the lipid moiety of a lipoprotein, fatty acid, phospholipid, cholesterol, cholesterol ester or triglyceride. As described above, the lipid oxidation activity of an abzyme may also lead to the oxidization of protein, carbohydrate and/or nucleic acid, for example the protein and/or carbohydrate moieties of a lipoprotein.

Chlamydial lipid oxidation is determined in some preferred embodiments because it provides for a convenient one step assay, which may be used to determine, for example, the presence or absence of an anti-Chlamydia abzyme. Oxidation of Chlamydial lipid will occur when a Chlamydia-specific antibody is present which binds and oxidises Chlamydial antigen comprising a lipid.

An atherosclerotic condition may be assessed in an individual by contacting a sample provided by an individual with a Chlamydial cell antigen; and determining the oxidation of lipid in said sample.

Determining the oxidation of the lipid may include determining the amount, level or degree of oxidation which is induced by contact with the Chlamydia antigen. Preferably, the Chlamydial cell antigen is a lipid antigen and the oxidation of the lipid antigen is determined.

An antigen may be purified and/or isolated or, more preferably, it may be comprised in a Chlamydia cell. An atherosclerotic condition in an individual may thus be assessed by contacting a sample provided by an individual with a Chlamydia cell; and determining the oxidation of the lipid of said cell.

The oxidation of lipid, for example in a sample, in the presence of the Chlamydia cell or antigen may be compared with the oxidation of lipid in the absence of the Chlamydia cell or antigen. An increase in lipid oxidation is indicative of the presence of an anti-lipid abzyme.

Lipid/lipoprotein peroxidation is a free radical chain reaction and is capable of self-propagation from one molecule to another, to a lipid-contained micelle, or to a whole cell (after attaching to its membrane via receptors or non-specific absorption) (Chemical and Biochemical Aspects of Superoxide and Superoxide Dismutase. Elsevier/North-Holland, New York, Amsterdam (1980); Lipid Peroxides in Biology and Medicine. Academic Press, Orlando, San Diego, San Francisco, New York, London (1982); Halliwell, B., and Gutteridge, J. M. C. Free Radicals in Biology and Medicine. Clarendon Press. Oxford (1996); Oxidants, Antioxidants, and Free Radicals. Taylor and Francis, Washington (1997)).

In some embodiments of the methods described herein, the propagation of peroxidation is used to facilitate the detection of lipid-oxidising abzymes.

For example, a microcontainer such as a liposome, vesicle or microcapsule which has a membrane which made of a material susceptible to free radical decomposition, for example a phospholipid membrane, may be loaded with a dye, fluorochrome or other reporter substance or detecting material, for example: Eosin, Fluorescamine, Rhodamine B or Malachite Green, and used in the detection of a lipid oxidising abzyme. Lipid oxidation in the methods described herein may thus be determined by determining the release of the encapsulated reporter substance.

The loaded microcontainer may be mixed with a sample of plasma or serum. A Chlamydia antigen, conveniently comprised in or part of a Chlamydia cell, is then added to the mixture. Any lipid oxidising abzymes in the sample then bind to the antigen and initiate peroxidation.

An atherosclerotic condition may be assessed by contacting a sample provided by an individual with a Chlamydial cell antigen in the presence of a microcontainer susceptible to lipid oxidation and containing a reporter substance; and determining the release of said reporter substance from the microcontainer.

Initiation of the lipid/lipoprotein oxidation by the interaction of Chlamydia antigen with an abzyme will self propagate and spread to the coating of the microcontainer. This damages the coating and causes the release of the reporter substance into the surrounding solution. This release is then detected.

If the intensity of the signal produced by the release of the reporter is not sufficient to cause a registerable or detectable signal, a free radical propagator or sensitiser can be included in the reaction mixture, for example: free ions and complexes of $Fe^{2+}/Co^{2+}$ or other metals of transient valence. These and other sensitizers serve to multiply the amount of free radicals in a system.

Release of incorporated material from the microcontainer leads to changes in the physical/chemical properties of the reaction mixture which can be registered visually (or by other conventional means) Alternatively, damaged/fragmented/dissolved microcontainers can be separated from unmodified ones either by active centrifugation or by passive sedimentation.

Instead of liposomes or other microcontainers (loaded with reporter substances), erythrocytes from the blood sample itself may be used as a target for the propagating lipid/lipoprotein peroxidation caused by anti-lipid abzymes. Chlamydia bacteria or antigens may be introduced or contacted with a blood sample, optionally in the presence of a sensitiser to ensure propagation of the peroxidation reaction. Lipid oxidation may be determined by determining the haemolysis of erythrocytes in the blood sample.

Any initiation of the lipid/lipoprotein oxidation by the interaction of Chlamydia antigen with abzyme in the sample will self propagate and spread to the erythrocyte cell membrane, leading to damage and eventually cell lysis. The appearance of haemolysis in the sample of the whole blood in response to the addition of Chlamydia bacteria/antigens is therefore indicative of the presence of lipid oxidising abzymes. Haemolysis may be determined by any suitable method.

An atherosclerotic condition may be assessed by contacting a sample provided by an individual and comprising erythrocytes with a Chlamydial cell antigen; and determining the haemolysis of said erythrocytes.

Liposomes or other microcontainers may be loaded with, for example, a material which can develop a color different to the red colour of haemoglobin. Alternatively, spinning of the tested samples or even passive sedimentation would separate undamaged microcontainers/erythrocyte. Release of reporter dye or haemolysis is indicative of the presence of lipid-oxidising antibodies in the analysed material. The intensity of the signal correlates with their activity/concentration.

Since whole blood may be analysed using the methods described above, they do not involve a centrifugation step and may be used in non-laboratory or domestic conditions. The presence or severity of atherosclerosis may, for example, be determined by comparing the observed reporter signal or haemolysis with known values in atherosclerosis patients and normal individuals. Such a comparison may be carried out using a chart, scale, graph or calibration which indicates the amount or level of reporter signal or haemolysis at particular stages or severities of atherosclerosis.

Lipid peroxidation is a redox process which may also be measured using a coupled redox system. suitable redox systems include physical and chemical systems. For example a sensor chip may be used to detect changes in the redox potential of a lipid oxidation reaction coupled thereto. A range of sensor chips based either on the redox enzymes or on the redox mediators are known in the art. Both of these types of sensors can be adjusted/used for the detection of free radical molecules or redox molecules coupled with them (Hall E. A. H. Biosensors. Redwood Press Ltd., Great Britain, 1990).

Accumulation of $H_2O_2$ produced by lipid peroxidation may be measured, for example, by addition of the coupled peroxidase-based reaction which will use hydrogen peroxide to oxidise its other co-substrate(s) and produce a colored product. An accumulation of $O_2^-$ produced by lipid peroxidation can be determined by using $O_2^-$-sensitive molecules, such as cytochrome C or riboflavin.

Alternatively, lipid peroxidation consumes molecular oxygen, hence any $O_2$-dependent chemical reaction or physical process can be used, for example, oxygen electrode or polarography. (Polarography. Ed. Kolthoff I. M., Lingane J. J. Interscience Publishers, New York, London, 19520

Aspects of the present invention will now be illustrated with reference to the accompanying figures described above and experimental exemplification and Tables below, by way of example and not limitation. Further aspects and embodiments will be apparent to those of ordinary skill in the art.

All documents mentioned in this specification are hereby incorporated herein by reference.

Table 1 contains data showing the effect of the IgG fraction extracted from human atherosclerotic lesion on lipid peroxidation of Chlamydia bacteria; pH 5,7; all measurements made in triplicate.

Table 2 contains data showing the cross-reactivity for lesion IgG between human serum lipoproteins and ovine strain of *Chlamydia psittaci;*

Table 3 contains data showing the effect of feline Chlamydia on lipid peroxidation in human serum; all measurements made in triplicate.

Table 4 contains data showing the role of IgG in the initiation of lipid peroxidation by ovine Chlamydia in human plasma; all measurements made in triplicate.

Table 5 contains data showing the effect of the addition of ovine Chlamydia into the control sera and in the sera of patients with clinical complications of atherosclerosis.

Table 6 shows the inhibition of lipid oxidizing activity of atherosclerotic lesion IgG by antioxidant inhibitors.

Table 7 shows examples of metal chelators which may be used in accordance with the present invention.

Table 8 shows examples of anti-microbials which may be used in accordance with the present invention.

Table 9 shows examples of anti-oxidants which may be used in accordance with the present invention.

Table 10 shows levels of lipid oxidising anti-Chlamydia antibodies in healthy and infected sheep (figures in brackets represent % increase/decrease against control).

Table 11 shows the inhibition of abymes using metal chelators.

Table 12 shows the inhibition of in vitro abzyme activity using metal chelators.

Table 13 shows the effect of aspirin on the activity of anti-Chlamydia abzymes in patients with Coronary Heart Disease.

Table 14 shows the effect of aspirin on the activity of anti-Chlamydia abzymes in patients with Silent Myocardial Ischaemia.

Table 15 shows abzyme activity in patients treated with anti-microbial agent.

Table 16 shows abzyme activity in patients treated with an anti-microbial agent plus aspirin daily.

Table 17shows the clinical condition of patients treated with anti-microbial agent only.

Table 18 shows average abzyme levels in groups of individuals suffering from atherosclerosis related conditions.

Table 19 shows individual abzyme levels in patients suffering from angina, who were either receiving or not receiving aspirin.

Table 20 shows the induction of abzymes in rabbits inoculated with Chlamydia.

Table 21 shows the effect of formalin treated Chlamydia in rabbits having induced abzymes.

Table 22 shows anti-Chlamydia abzyme activity in patients treated by azithromycin, 500 mg daily (therapy group A).

Table 23 shows anti-Chlamydia abzyme activity in patients treated by azithromycin, 500 mg, plus aspirin, 250 mg, daily (therapy group B).

Table 24 shows anti-Chlamydia abzyme activity in patients treated by azithromycin, 500 mg daily plus antioxidants (therapy group C).

Table 25 shows anti-Chlamydia abzyme activity in therapy group D patients treated by aspirin, 250 mg daily (therapy group D).

Table 26 shows anti-Chlamydia abzyme activity in the patient control group.

Table 27 shows a summary of the results of anti-abzyme therapy.

Table 28 shows an evaluation of the severity of angina pectoris by modified Rose-Blackburn Questionnaire before and after treatment.

Table 29 shows abzyme and Rose-Blackburn Test scores before and after treatment for IRD patients who tested negative for anti-Chlamydia IgG.

Table 30 shows the inhibitory properties of azithromycin on abzymes

Table 31 shows the effect of various drugs on anti-Chlamydia abzyme activity.

Table 32 shows the effect of anti-abzyme therapy on thrombosis and blood clotting.

Experiments

Materials and Methods

Samples 3 samples of sera were used from 22 patients with clinical complications of atherosclerosis admitted for coronary artery and abdominal aorta by-pass operations in the Cardio-Vascular Surgery Centre of the Clinical Hospital No.1 in Rostov-na-Donu, Russia.

20 of these patients were male and 2 female, aged between 47 and 66. One of these patients, No.6/6a had an acute myocardial infarction at the moment of the testing, hence in some final calculations the data from this patient were not included. The control group was comprised of clinically healthy volunteers 5 of whom were male and 5 female aged between 40 and 55.

Pieces of atheromas from abdominal aorta from 7 of these patients were used to extract IgG fraction by a protein A sorbent as described below.

Extraction of IgG from Atherosclerotic Lesion

The pieces of aorta (approximately 200-400 mg wet weight) were cut into pieces of approximately 10 mg each, placed in 5.0 ml of PBS with 1% non-ionic detergent Igepal CA-630 and homogenized by a mechanical homogenizer (Ul-tra-Turrax) at full-power with a 15 mm probe three times for 3 seconds each with 20 second cooling intervals. After homogenization the insoluble components were separated by centrifugation at 5000 g for 10 minutes and supernatants were used for analysis.

The supernatant was treated with protein A attached to cross-linked 4% beaded agarose at 37° C. for 30 minutes. The immunoglobulin fraction attached to the beads was then spun down at 5000 g for 10 minutes and the supernatant decanted. In order to remove any lipoproteins attached to the sedimented immunoglobulins, the samples were re-suspended with 10% of Igepal CA-630. They were then centrifuged at 5000 g for 10 minutes and the supernatant was decanted.

To remove the detergent three subsequent washings were performed in the excess of the phosphate buffer with centrifugation under the same regime. The removal of lipoprotein from the immunoglobulin fraction was confirmed by the absence of cholesterol in this fraction.

Determination of Anti-Chlamydia Abs

Blood was collected from an ante-cubital vein in the morning after an overnight fast, serum was separated and frozen at −20° C. prior to being tested.

The presence of anti-Chlamydia antibodies was measured in the agglutination reaction with ovine Chlamydia cells and by ELISA (recombinant antigen-based) assays.

For the agglutination reaction, gradual dilutions of the tested sera were incubated for 24 hours at 37° C. with $10^6$ of live ovine Chlamydia. The appearance of aggregates was detected and estimated at 700 nm. The ELISA assay was performed in accordance with manufacturer's instructions (Medac).

A titre$\geq$1:64 was considered to be seropositive.

Determination of Peroxidation of Lipids

Lipid peroxidation was assessed as a level of MDA concentration which was measured by spectrophotometric method [Draper, H. H. et al Free Radic. Biol. Med. (1993) 15, 353]. This method is based on the formation of a colored product when malondialdehyde reacts with thiobarbituric acid.

Cross Reactivity between Serum Lipoproteins and Chlamydia

The IgG fraction comprising anti-Chlamydia abzymes was extracted from a human atherosclerotic lesion as described above. 100 μl of this fraction (containing 1 μg/ml) was pre-incubated with 890 μl of whole or delipidated serum from a healthy donor for 1 hour at 37° C.; pH 5.7.

Lipoproteins (and associated material) were removed from the serum by preparative ultra-centrifugation in KBr solution in accordance with the earlier described method [Havel R. J et al. J. Clin. Invest. (1955) 34, 1345-1353.22].

$10^5$ *Chlamydia psittaci* cells (Intervet) in a 10 μl volume were then added to the serum. The amount of oxidation induce by contact with the Chlamydia cells was then determined using the method described above.

In the presence of binding between the anti-Chlamydia abzymes and the plasma lipoproteins, no additional oxidation on contact with the Chlamydia cells is observed, because the anti-Chlamydia abzymes are removed by the ultracentrifugation.

In the absence of binding between the anti-Chlamydia abzymes and the plasma lipoproteins, oxidation is observed on contact of the plasma with the Chlamydia cells, because the anti-Chlamydia abzymes are still be present in the sample.

Assay for Anti-Chlamydia Abzymes

Reagents used in assaying anti-Chlamydia abzymes are as follows;

1. Live ovine Chlamydia (lyophilised form)
2. PBS (to dissolve bacteria)
3. 0.05M acetate buffer pH 4.0
4. 40% trichloroacetic acid
5. 1 mM 2-thiobarbituric acid.

The presence or amount of catalytic anti-Chlamydia antibodies in a sample was detected as follows;

1. Samples of tested sera are diluted 1:1 by 0.05M acetate buffer pH 4.0 to make the final pH of these samples between 5.6-5.8.

2. 990 µl of the diluted serum mixed with 10 µl of the commercial live ovine Chlamydia vaccine.
3. Samples are then incubated overnight (12-16 hours) at 37° C.
4. To each sample 250 µl of 40% trichloroacetic acid and 250µl of 1 mM 2-thiobarbituric acid are added.
5. All samples are placed in a water bath and boiled for 30 minutes.
6. Samples are cooled down and centrifuged at 3,000 g for 10 minutes.
7. Supernatants are collected and their absorption is measured at λ 525 nm to determine the concentration of malondialdehydes (MDA) which are products of lipid peroxidation.

Results

EXAMPLE 1

IgG was extracted from an atherosclerotic lesion in a patient using the method described above. Anti-Chlamydia antibodies were found to be present in this IgG fraction (FIG. 1).

Figure 2:
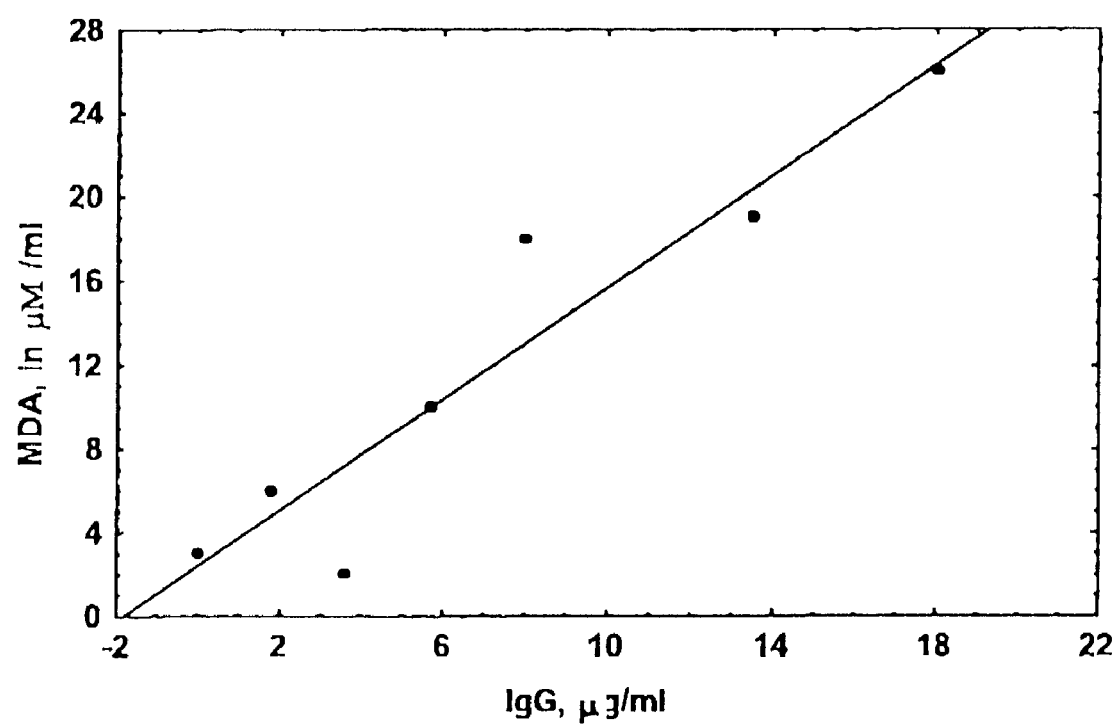
FIG. 2 shows the dependence of ovine Chlamydia peroxidation on the concentration of human atherosclerotic lesion IgG. Concentration of Chlamydia was constant and the pH was 5.7.
Figure 3:
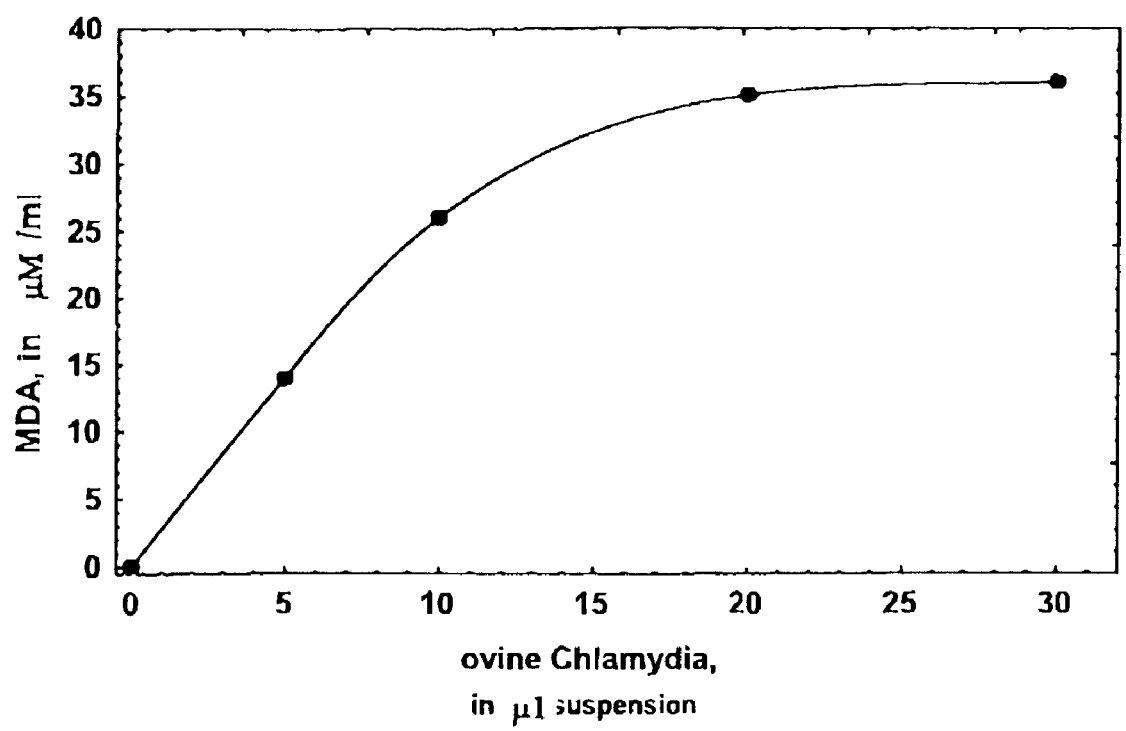
FIG. 3 shows the Michaelis-Menten kinetics of lipid peroxidation in ovine Chlamydia by 1.8 μg human atherosclerotic lesion IgG; apparent $K_M$=13.3-16.1 μl of Chlamydia suspension; pH 5.7.
Figure 4:
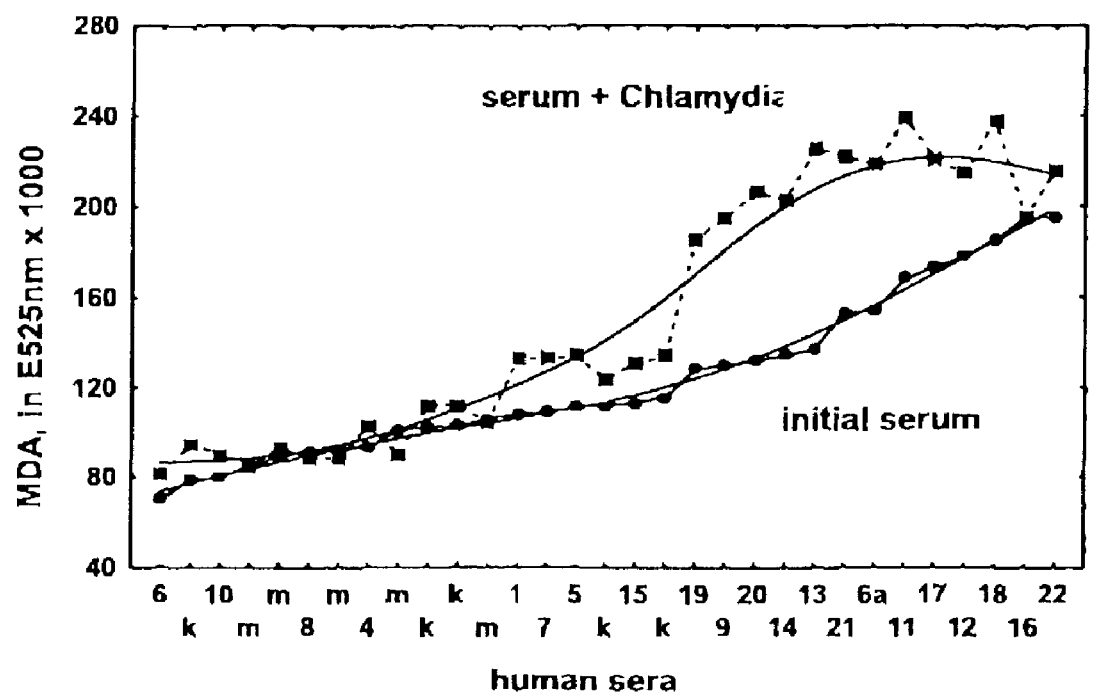
FIG. 4 shows the effect of the addition of ovine Chlamydia suspension on lipid peroxidation in human serum. 10 μl of the bacterial suspension was added to 990 μl of the diluted 1:1 serum; pH 5.7; all the mixed samples were incubated at 37° C. for 18 hours (numbers of sera are the same as in table 5).

The ability of the extracted IgG fraction to oxidize lipid was determined. The IgG fraction was shown to cause a peroxidation of lipids in both ovine and feline strains of *Chlamydia psittaci* (table 1). Kinetic analysis of this peroxidation reaction showed that the reaction had an enzymatic character (FIGS. 2, 3). *Chlamydia bacterium* can therefore be considered as a substrate for their antibodies extracted from human atherosclerotic lesion.

The epitopes for anti-Chlamyidia abzymes were investigated further using non-ionic detergents. Treatment of Chlamydia with Triton X-100 or Igepal CA-630 abolished the oxidation of the lipids in the bacteria by the extracted abzymes. Similar results were obtained for the treatment of human serum low density lipoproteins.

This provides indication that either the epitopes for the catalytic antibodies are conformational and/or the integrity of the antigen is important to initiate the oxidation of lipids in both lipoproteins and Chlamydia.

The ability of anti-Chlamydia abzymes to cross-react with plasma lipoproteins was then determined. IgG extracted from atherosclerotic lesion was pre-incubated with serum from a patient to allow anti-lipoprotein antibodies in the extract to interact with non-modified lipoproteins. The lipoproteins and antibodies bound thereto were then removed by ultra-centrifugation.

Catalytic anti-Chlamydia antibodies were found to be removed with the lipoprotein (Table 2). This demonstrates that the catalytic anti-Chlamydia antibodies cross-react with both serum lipoproteins and the ovine strain of Chlamydia bacteria.

The presence of anti-Chlamydia antibodies in the serum of atherosclerosis patients was then investigated. The addition of ovine Chlamydia to the serum of the patients was observed to cause an increase in lipid peroxidation within the sample. A similar effect was observed with a feline Chlamydia strain (table 3).

The observed effects were due to presence of lipid oxidising anti-Chlamydia antibodies in the fraction of IgG in patient sera (table 4). Catalytic antibodies from the serum of atherosclerosis patients were therefore observed to cross-react with both lipoproteins and ovine Chlamydia.

Correlative analysis of the concentration of anti-Chlamydia and anti-lipoprotein antibodies in human sera showed that both these parameters have a statistically significant positive link with the high correlation coefficient 0.82. This provides further indication that the same antibody possesses both binding activities.

In studies, with atherosclerosis patients using the assay method described above, catalytic anti-Chlamydia antibodies were found in 81% of the patients with clinical complications of atherosclerosis and only in 10% of the control group (FIG. 4, table 5). This demonstrates that these antibodies are a pathogenic marker of this disease.

This study demonstrates for the first time the existence of anti-lipids/lipoproteins abzymes in biological systems. Their occurrence in atherosclerosis but not in the norm indicates that these abzymes play an important role in the pathogenesis of this disease and its complications. It can also interlink such main biochemical/immunological disorders as the activation of lipid peroxidation, the occurrence of anti-lipoprotein antibodies and Chlamydia infection, all of which are involved in the development of atherosclerosis.

The presence of lipid-oxidising anti-Chlamydia antibodies in the plasma of an individual indicates that the pathological changes specific for this disease have already started. Since these abzymes are responsible for a lipid/lipoprotein oxidation and this process usually correlates with the degree/intensity of generalisation of atherosclerosis, the level/activity of anti-lipid-abzymes reflects the severity of this disease.

Changes in the lipoprotein profile and the elevation of the total cholesterol in plasma/serum are the only specific risk factors established for atherosclerosis. However, these changes can be detected for only 10-15% of all patients with clinical complications of this disease. Detection of lipid-oxidising anti-Chlamydia antibodies is the second specific marker for atherosclerosis, but has a much higher diagnostic value than the measurement of the lipid parameters described above.

The methods herein are therefore widely applicable in the diagnosis and prophylaxis of atherosclerosis and related conditions.

EXAMPLE 2

Inhibition of Lipid Peroxidation

Human Specimens

Antibodies were extracted from advanced atherosclerotic lesions of human aorta retrieved from four male patients, age range 53-64, during bypass surgery of an abdominal aortal stenosis at the Centre of Cardio-Vascular Surgery of Clinical Hospital No.1 in Rostov-na-Donu, Russia. After recovery these samples were immediately put in 30% w/v solution of NaCl and stored at 0-4° C. for 1-2 weeks prior to examination.

In control experiments, it was shown that during this period the activities of such enzymes as trypsin, catalase, superoxide dismutase, glutathione peroxidase, creatine kinase and lactate dehydrogenase, together with a level of immunoglobulin (IgG) fragmentation and the degree of lipid peroxidation (concentration of malonaldehydes) did not significantly change.

The pieces of aorta (approximately 200-400 mg wet weight) were cut into pieces of approximately 10 mg each, placed in 5.0 ml of PBS with 1% non-ionic detergent Igepal CA-630 and homogenized by a mechanical homogenizer (Ultra-Turrax) at full-power with a 15 mm probe three times for 3 seconds each with 20 second cooling intervals. After homogenization the insoluble components were separated by centrifugation at 5000 g for 10 minutes and supernatants were used for analysis.

Antibody Extraction The antibodies were extracted and analysed separately from the lesions of the four pieces of the abdominal aorta obtained from the four different patients.

The first step was the treatment of the supernatant with protein A attached to cross-linked 4% beaded agarose at 37° C. for 30 minutes. After that the immunoglobulin fraction attached to the beads was spun down at 5000 g for 10 minutes. The supernatant was decanted. In order to remove any lipoproteins attached to the sedimented immunoglobulins, the samples were re-suspended with 10% of Igepal CA-630. They were then centrifuged at 5000 g for 10 minutes and the supernatant was decanted. To remove the detergent three subsequent washings were performed in the excess of the phosphate buffer with centrifugation under the same regime. The removal of lipoprotein from the immunoglobulin fraction was confirmed by the absence of cholesterol in this fraction.

Lipoproteins

Low density lipoproteins, d=1.030-1.050, were obtained from the plasma of healthy donors by sequential preparative ultracentrifugation in KBr solution in accordance with the earlier described method [Havel R. J. et al J. Clin. Invest. (1955) 34, 1345-1353]. LDL can be already associated with plasma immunoglobulins in these preparations [Bauer B. J. et al Atherosclerosis (1982), 44, 153-160].

These immunoglobulins can potentially either interfere with a reaction between LDL and their antibodies attached to the protein A, or can be bound by the latter protein itself. To avoid these possible artefacts, it was important, before the titration of lipoproteins with lesion antibodies in the affinity tests, to remove LDL with antibody attached using a saturated amount of protein A agarose beads.

In order to determine the level of LDL (in terms of cholesterol concentration), the calibration curve was made for every new batch of lipoproteins and during every new experiment.

LDL Peroxidation by Lesion IgG.

Samples of LDL with or without (control) tested antioxidants were incubated with lesion IgG for 16 hours at 37° C. at pH 5.6. The level of lipid peroxidation, in terms of the concentration of malondialdehyde (MDA), was measured by the following procedure. To 1.0 ml of each sample were added 250 µl of 40% trichloroacetic acid and 250 µl of 1 mM 2-thiobarbituric acid. After boiling the samples in a water bath for 30 minutes, they were cooled down and centrifuged at 3,000 g for 10 minutes. Supernatants were collected and their absorption measured at λ 525 nm.

The results of this experiment are presented in Table 6.

A range of inhibitors with antioxidant activity were observed to reduce the lipid oxidation activity of antibodies isolated from atherosclerotic plaques below the limit for detection in this assay. All these compounds therefore inhibit the activity of lipid oxidizing antibody.

Isolated abzymes were assayed in vitro for catalytic activity as described herein in the presence various anti-oxidant inhibitors of the following classes:

Iron (Fe2+) chelators—tetracycline
Copper (Cu2+) chelators—DDC, aspirin and penicillamine
General metal chelators—CN—, N3, DTPA (chelates free ions only) and picolinic acid.

Results are shown in Table 11.

These results show that abzyme inhibition occurs through copper chelation rather than iron chelation. Three separate copper chelators were demonstrated to block activity and these results suggest that the abzymes contact a bound copper ion as catalytic centre.

EXAMPLE 3

Clinical Example of Reduction in Lipid Oxidising Anti-Chlamydia Antibody Activity Patient—A. M. P., Caucasian, male, 43 years old, having clinical symptoms resembling the early stages of angina pectoris with complaints of transient unprovoked chest pain in combination with breathlessness. However, an ECG revealed no pathological changes in the heart.

The results of a blood test on Dec. 27, 2000 revealed normal total cholesterol and LDL-cholesterol levels; titers of anti-Chlamydia IgG and IgA antibodies were both 1:64 (ELISA, Medac). However, lipid-oxidising anti-Chlamydia abzymes were detected and their activity was 32 µM MDA (mean figure of triplicate measurement) per 1 ml of his serum.

The following daily treatment, over the course of three months, was recommended: Tetracycline hydrochloride 500 mg, in combination with an antioxidant cocktail—Vitamin E 20 mg, Vitamin A 1.5 mg, Vitamin B6 3.2 mg, Ascorbic acid 180 mg, Zinc Gluconate 30 mg, L-Selenomethionine 100 µg per.

In three months after the beginning of the therapy complaints of chest pain and breathlessness disappeared. At the end of March, at the end of the treatment and almost exactly 3 months after treatment started, the analysis of his serum showed no changes in anti-Chlamydia IgG and IgA antibody titers (1:64 (ELISA, Medac)). At the same time the presence of anti-Chlamydia abzymes was not detectable.

Two weeks later the test was repeated with the same result.

EXAMPLE 4

The Influence of Ovine Chlamydia on Lipid Peroxidation of Ovine Sera

Sheep were vaccinated with Chlamydial cells using standard techniques and tested for abzyme activity. The results are set out in Table 10.

Pre-vaccinated sheep were disease-free and healthy and showed no significant changes between assay levels with and without Chlamydia.

Post-vaccination, sheep showed very high levels of anti-chlamydia antibodies but insignificant/no levels of abzymes.

Post abortion (wild type) represents sheep with Chlamydiosis disease which have aborted due to the occlusion of the vascular system in the uterus: in these, the level of abzyme activity verified by the addition of Chlamydia is significantly higher than without Chlamydia.

These results show that administration of Chlamydial vaccine may reduce or prevent the production of lipid oxidising antibodies.

EXAMPLE 5

The Association of Abzyme Activity and Arterial Stenosis

The activity of lipid-oxidising anti-Chlamydia antibodies and the degree of arterial stenosis in two different clinical groups was investigated. The first was a group of patients with Ischaemic Heart Disease (IHD) and the second a group of patients with Ischaemic Cerebrovascular Disease (TCD).

Coronary Artery Stenosis

Figure 5:
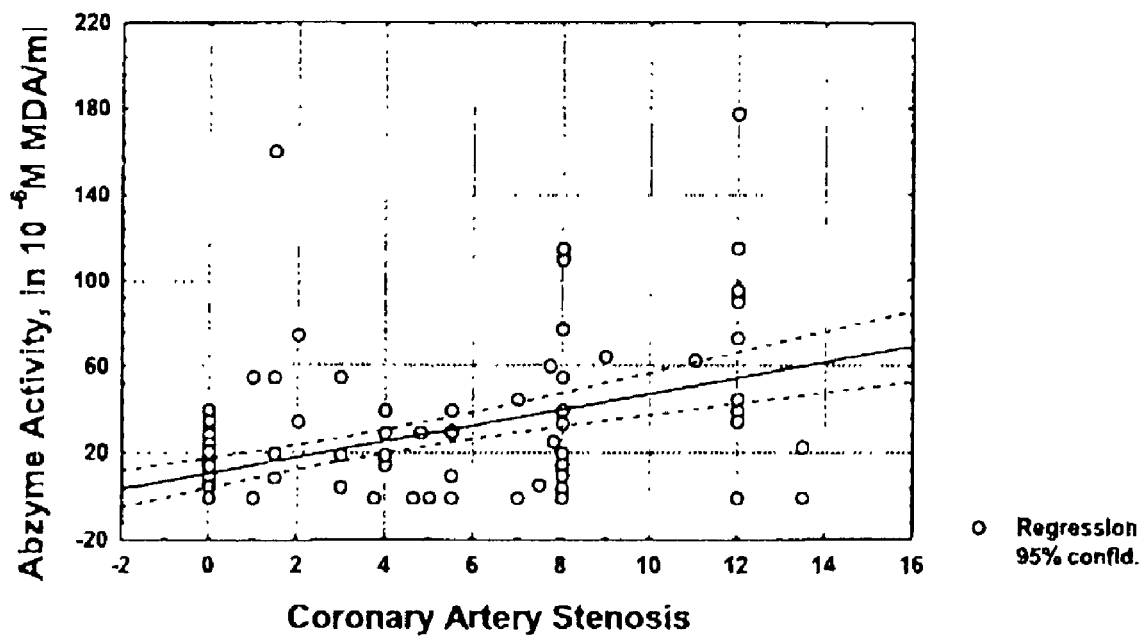
FIG. 5 shows the correlation between the degree of coronary artery stenosis and the activity of lipid-oxidising anti-Chlamydia antibodies in IHD patients. Severity of the stenosis is presented in terms of a score, which was calculated as an integral parameter of the stenosis of coronary arteries estimated by angiography.

The preliminary results of the trial show a positive and significant correlation between the activity of the anti- Chlamydia abzymes and the severity of the stenosis of coronary arteries of patients with IHD (FIG. 5).

Figure 6:
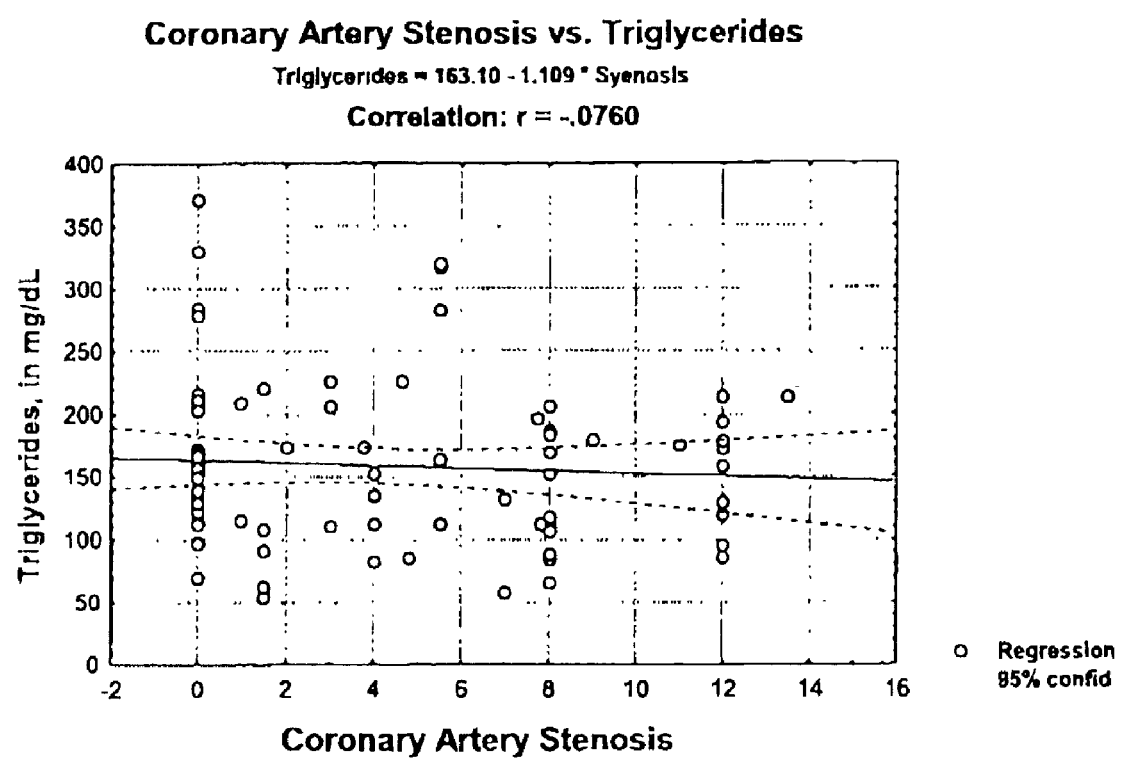
FIG. 6 shows the relationship between the degree of coronary artery stenosis and triglycerides concentration in IHD patient sera.
Figure 7:
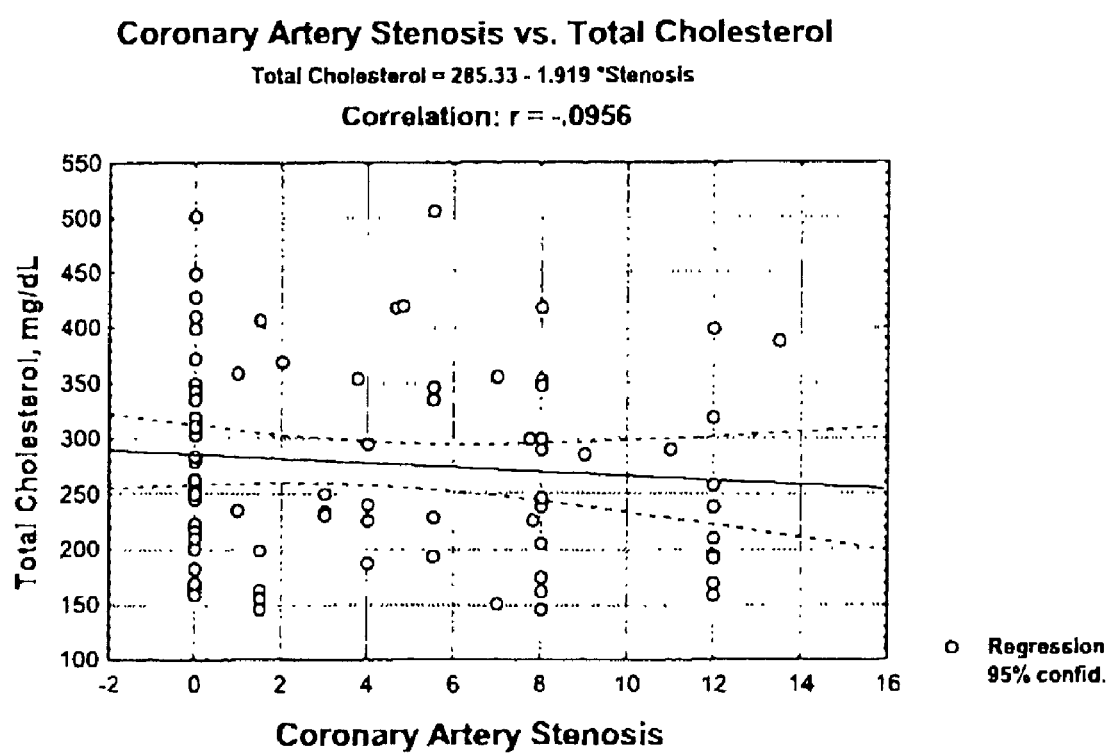
FIG. 7 shows the relationship between the degree of coronary artery stenosis and total cholesterol concentration in IHD patient sera.
Figure 8:
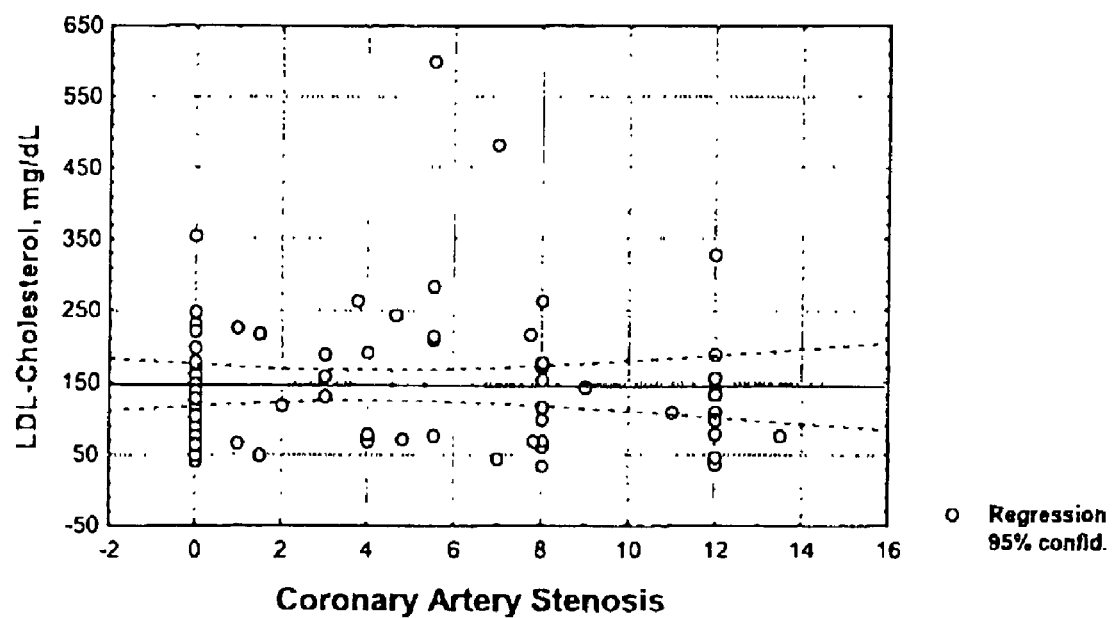
FIG. 8 shows the relationship between the degree of coronary artery stenosis and LDL-cholesterol concentration in IHD patient sera.

No links was observed between the degree of coronary stenosis and such serum lipids as triglycerides, total cholesterol and cholesterol of low density lipoproteins, LDL-cholesterol (FIGS. 6, 7, 8)

Cerebral Artery Stenosis

Figure 9:
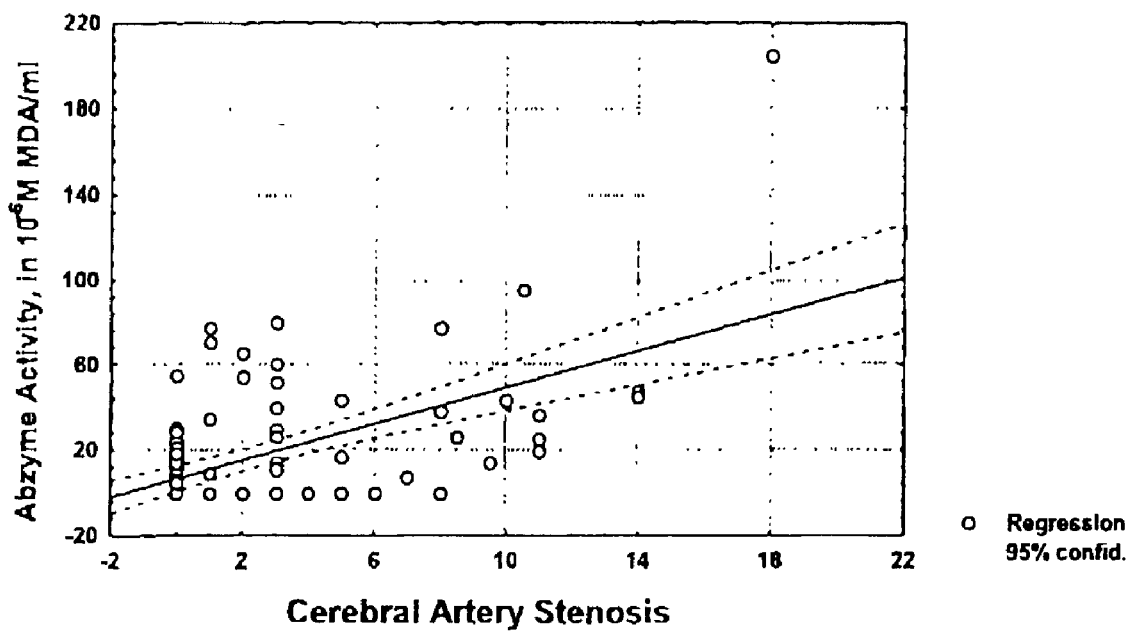
FIG. 9 shows the correlation between the degree of cerebral artery stenosis and the activity of lipid-oxidising anti-Chlamydia antibodies in ICD patient sera. Severity of the stenosis is presented in terms of a score, which was calculated as an integral parameter of the stenosis of cerebral arteries estimated by angiography.

A positive significant correlation between level of the abzymes and arterial stenosis was observed in the group of patients with ICD (FIG. 9).

Figure 10:
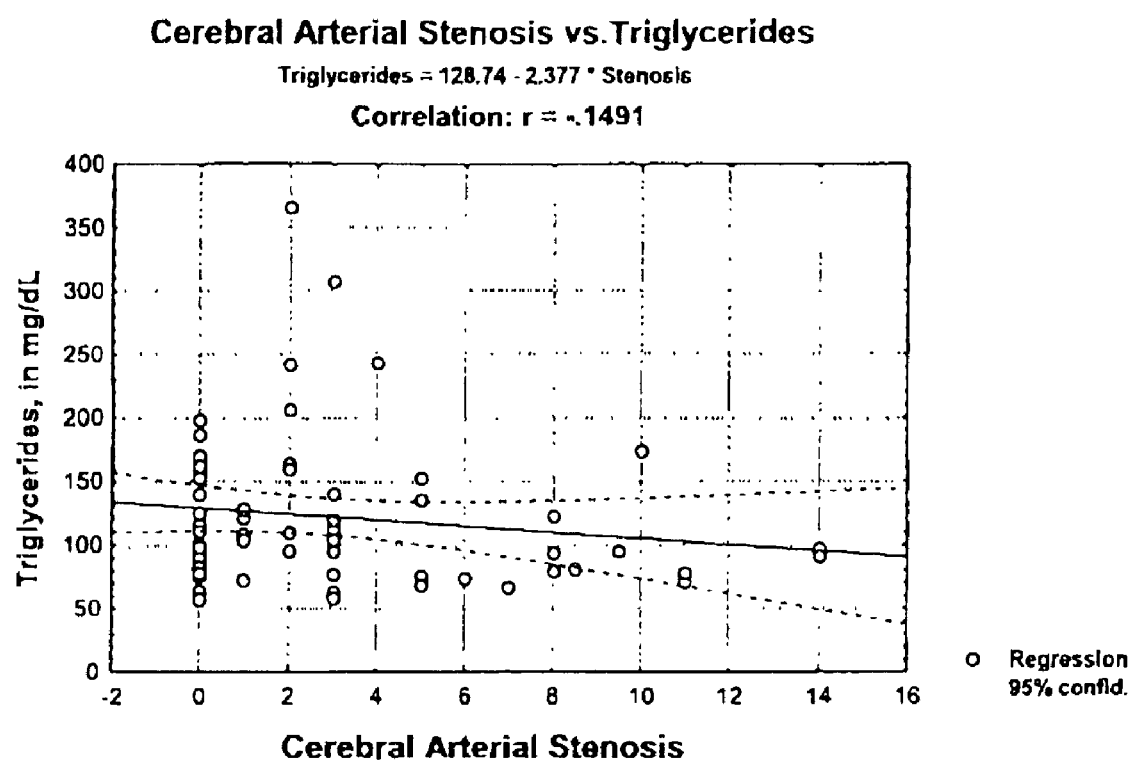
FIG. 10 shows the relationship between the degree of coronary artery stenosis and triglycerides concentration in ICD patient sera.
Figure 11:
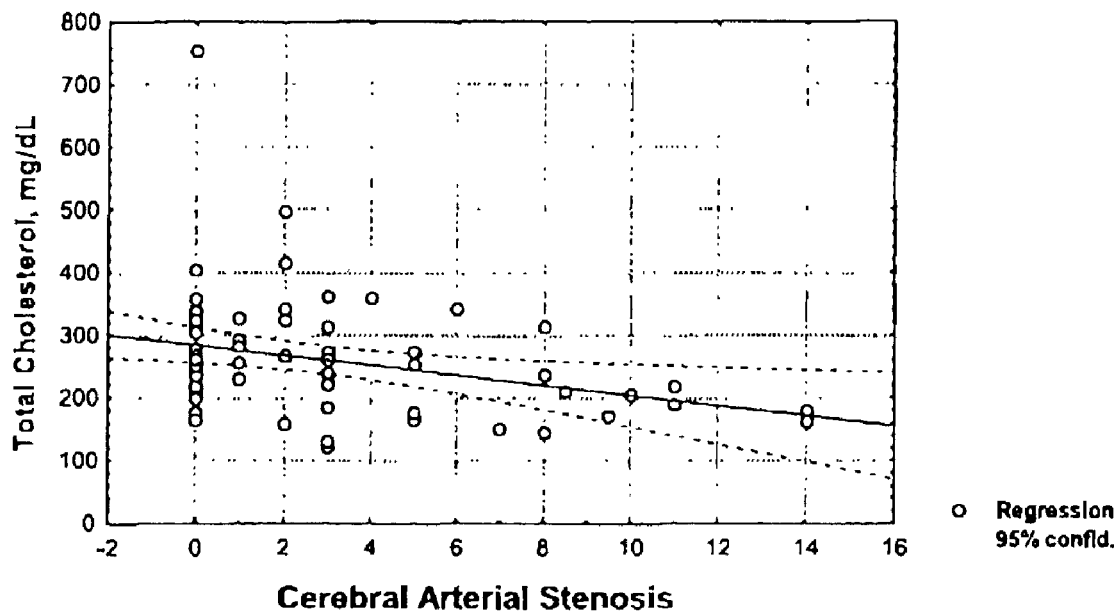
FIG. 11 shows the relationship between the degree of coronary artery stenosis and total cholesterol concentration in ICD patient sera.
Figure 12:
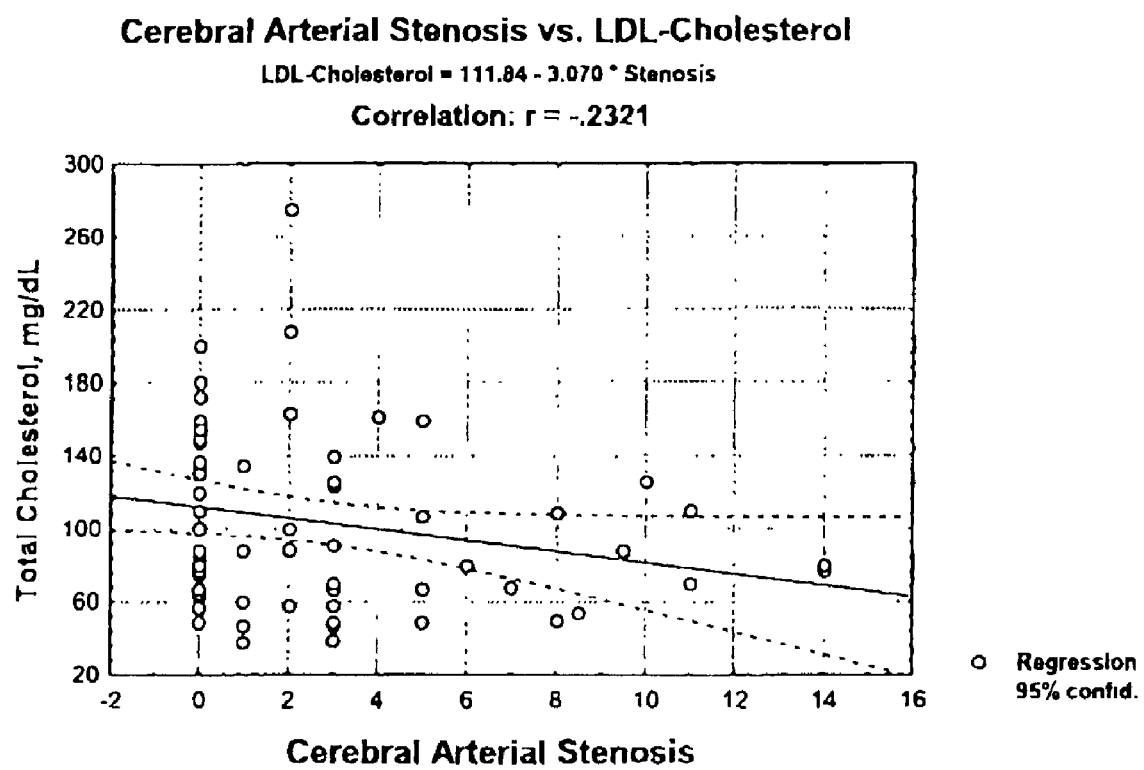
FIG. 12 shows the relationship between the degree of coronary artery stenosis and LDL-cholesterol concentration in ICD patient sera.

As in the IHD patients, in this group there no links were found between the degree of arterial stenosis and serum triglycerides, total cholesterol and LDL-cholesterol (FIGS. 10, 11, 12).

These experiments establish a positive link between anti-Chlamydia abzyme activity and the degree of stenosis both in heart and brain arteries, and shows that these antibodies are involved both in the initiation and progression of atherosclerosis.

EXAMPLE 6

Inhibition of Abzymes Using Acetylsalicylic Acid (Aspirin)

The data presented in Tables 13 and 14 demonstrate that the activity of anti-Chlamydia lipid oxidising abzymes can be inhibited by acetylsalicylic acid (aspirin) when it is administered to humans. Three patients with Coronary Heart Disease (CHD), whose blood had a significant level of abzyme activity of these abzymes, were treated with 250 mg daily dose of aspirin.

After a week, blood tests of these patents revealed a significant inhibition of the abzyme activity: 5-fold for the one patient and an undetectably low level for the other two (Table 13).

To eliminate the possibility that administration of aspirin in the above experiments coincided with the natural clearance of the abzymes from the bodies of the patients and to investigate the in vivo effect of aspirin on anti-Chlamydial lipid oxidising abzymes, the following experiment was undertaken.

A patient F with Silent Myocardial Ischaemia who was taking regularly 250 mg aspirin daily was identified. The level of the abzymes in the blood of patient F was determined and found to be almost undetectable.

Patient F stopped taking aspirin for a week and the level of abzyme in his blood was determined again. A significant level of lipid oxidising abzymes was found in the serum of patient F.

Patient F resumed the previous regime of 250 mg aspirin daily, and the level of abzymes was determined after 7 day. The level of these abzymes was significantly reduced (Table 14) relative to the level when the patient was not receiving aspirin.

During the course of theses experiments, the patient did not have any respiratory disorder, or signs of any other pathological conditions. This indicates that the recorded variations of the abzyme activity were related to the intake of aspirin by this patient.

In conclusion, the present data show that acetylsalicylic acid inhibits lipid-oxidising anti-Chlamydia antibodies in vivo, and, in particular, in patients with clinical complications of atherosclerosis.

EXAMPLE 7

Antibodies which Cross-React with Chlamydial Cells

A commercially available preparation of antibodies specific for human Apo-B was tested for ability to cross-react with ovine *Chlamydia psittaci* (Intervet).

The anti-apo-B antibody preparation was observed to contain a fraction which also binds to ovine Chlamydia (FIG. 13).

Apo-B therefore has an epitope which is identical to an epitope present on the Chlamydial membrane. Antibodies which bind this epitope will cross-react with Chlamydia cells and human apo-B.

EXAMPLE 8

The Effect of Anti-Chlamydial Agents on Abzyme Activity in vivo

Patients aged between 45 and 62, with stable angina were treated either with 500 mg azithromycin once per day for 15 days and 30 days or with 500 mg azithromycin, 500 mg, plus aspirin, 250 mg, daily for 15 days.

Abzyme activity before and after treatment is shown for the first group in Table 15 and for the second group in Table 16.

Abzyme activity was shown to be significantly reduced in both groups of patients after 15 days, with the reduction being particularly large in the group treated with azithromycin and aspirin. A reduction in LDL levels was also observed. No adverse reactions were registered in any of the patients.

The clinical condition of patients was also observed to improve over the course of treatment (Table 17).

Administration of the anti-Chlamydial drug azithromycin over two weeks, in particular in combination with aspirin, reduced abzyme activity and improved the clinical condition of patients suffering from angina.

EXAMPLE 9

Abzyme Activity in vivo

Abzyme levels were determined in five sets of people using the methods described herein. A control group were determined to be healthy by present techniques. A silent ischaemia group were individuals who were shown to be ischaemic in an exercise/ECG test but were unaware of any health problems. Groups of individuals suffering from stable or unstable angina and who had suffered a myocardial infarction were also tested.

The average level of abzymes in each group is shown in Table 18, where n is the number of individuals in each group. Individuals were considered to be positive for abzymes, if a 15% increase in lipid oxidation was observed on addition of Chlamydia cells using the methods described herein. The percentage of each group who were positive for abzymes is also shown in Table 18. None of the values in the table has been adjusted for individuals taking aspirin.

The level of abzyme activity and the proportion of individuals testing positive for abzymes is shown to correlate with the severity of the individual's condition. Abzyme activity is observed to drop sharply after a heart attack (compare values for unstable angina and acute phase myocardial infarction). Abzyme activity then rises progressively after the heart attack in surviving patients.

This is indicative of an active role for abzymes in the induction of a myocardial infarction. Abzymes may form part of the agglutination mechanism of the thrombolytic clots which block blood vessels and produce the infarction. This agglutination into clots reduces the detectable abzyme activity in the vascular system. As the clot dissolves post-infarction, detectable abzyme activity increases.

EXAMPLE 10

The Effect of Aspirin on Abzyme Activity in vivo

Abzyme activity was determined in groups of individuals with class I, II and III stable angina or unstable angina using the methods described herein. Individuals were also questioned as to whether they were taking aspirin. Individuals were sub-grouped according to whether they reported taking aspirin and the results are shown in Table 19. These results are not adjusted for individuals taking aspirin but not reporting it.

The figures shown in Table 19 are values of abzyme activity of individuals in each group (i.e. class I aspirin takers and non-aspirin takers etc).

These results show that abzyme levels correspond to the severity of the disease. Aspirin takers generally have lower abzyme activity than non-aspirin takers with the same clinical symptoms.

EXAMPLE 11

Animal Model for Atherosclerotic Disorders

Rabbits were infected with *Chlamydia psittaci* (Lori strain) by the intra-tracheal route with 1.5 mls of 10% suspension of chicken embryo containing $1 \times 10^{7.5}$ of Chlamydia cells. The sera of the rabbits was collected at day 0 (pre-infection) and then every 14 days thereafter, by using the standard blood collection route from the heart.

The sera was then used in a standard ELISA assay to measure the titre of anti-Chlamydia IgG. On the same hera samples, the amount of Chlamydia abzyme level was measured using the standard assay described previously. The appearance of abzymes correlates with the appearance of anti-Chlamydia IgG antibodies.

Results for 4 rabbits (3 infected and 1 control) are shown in Table 20.

These results show that an animal model with high abzyme levels can be generated by infection with Chlamydia. These models are useful in following the progression of disease caused by abzymes and determining various parameters such as rate of clearance. Models are also useful in testing compounds as potential drugs for the reduction of abzyme levels and concomitant improvement in symptoms.

EXAMPLE 12

Anti-Chlamydia Abzymes in Rabbits

The production of lipid-oxidising anti-Chlamydia antibodies was demonstrated using a rabbit model produced as described above by intra-tracheal infection with *Chlamydia Psittaci*.

Results are shown in Table 21. Rabbits were infected intra-tracheally with 1.5 ml of 10% suspension of chicken embryo containing $1 \times 10^{7.5}$ of *Chlamydia Psittaci* (Lori strain) and blood was collected from the rabbit hearts. Abzyme levels on $7^{th}$ day after a subcutaneous injection of a vaccine, formalin treated $1 \times 10^{7.5}$ *Chlamydia Psittaci* (Lori strain) are shown (§ table 21).

The appearance of abzymes coincided with the accumulation of anti-Chlamydia IgG detected as detected by ELISA. An injection of the same bacteria, but in formalin treated preparation, on the $14^{th}$ day of the infection (rabbit 3) led to an increase in the ELISA anti-Chlamydia IgG titers on the $7^{th}$ day after this inoculation. At the same time, in the serum of this rabbit there was a 2-fold reduction in the abzyme activity, from 131 to 64 µM MDA/ml.

There was no such reduction in the abzyme activity registered for two other rabbits, which did not receive this inoculation. Inoculation of the vaccine preparation of the Chlamydia antigen was thus observed to reduce the presence/activity of anti-Chlamydia abzymes.

EXAMPLE 13

Anti-Abzyme Therapy in Ischaemic Heart Disease

A group of 30 patients with ischaemic heart disease (IHD) was selected for experimental therapy to reduce/eliminate the activity of anti-Chlamydia abzymes in their serum (the therapy group) and a group of 20 'matched' patients were not treated (the untreated Patient Control Group). The trial took place in Saratov Cardiological Centre (Russian Federation) from June until August 2002.

The therapy group comprised 23 male and 7 female patients with an average age of 55±1.1 years. The patients control group for monitoring of the abzyme level comprised 20 patients with IHD, of which 15 were male and 5 were female patients with an average age of 53±1.2 years. Each patient gave written consent for his/her participation in the trial.

All patients had angina of II-III class of Canadian Cardiological Society classification. 15 patients in the therapy group and 10 in the patient control group had a history of myocardial infarction in the past year. IHD diagnosis for the other 15 patients in the first group and 10 in the patient control group was confirmed by coronary angiography, which detected 70% or more of arterial stenosis.

Apart from the degree of the generalization or severity of atherosclerosis, all groups were matched not only on age, gender and risk factors but also on medication, nitrates, β-blockers, angiotensin-converting enzyme inhibitors etc.

The progression of the clinical condition of the patients was monitored by the use of the modified Bruce Protocol for treadmill exercise/stress ECG testing and on the Rose-Blackburn Questionnaire (Cardiovascular Survey Methods. WHO, Geneva, 1968).

The main parameter of the selection of a patient for the trial was a level of anti-Chlamydia abzyme activity in excess of 15 µM of malondialdehyde (MDA) per ml of serum. The therapy group was split into 4 therapeutic sub-groups:

1) Therapy group A.—those given a nonspecific inhibitor of anti-Chlamydia abzymes, azithromycin, which also has anti-microbial properties, was prescribed in the dose of 500 mg daily.
2.) Therapy group B—a combined administration of azithromycin, in the same dose, with acetylsalicylic acid (aspirin) was prescribed. The latter has the apparent ability to block specifically the abzymes via chelating ions of copper in their active centre. The dose of aspirin was 250 mg per day.
3.) Therapy Group C—a combined administration of two types of nonspecific inhibitors of the abzymes with anti-oxidant properties, anti-microbial azithromycin, in the same dose as in the previous groups, and vitamins E, A, C, was prescribed. The daily dose of vitamin E was 30 mg, vitamin A 1,500 EU and vitamin C 90 mg.

4.) Therapy Group D—The patients in this group were given 250 mgs aspirin daily only.

The blood of the patients of all three groups was tested every two weeks. The therapies were continued subject to the efficiency of the suppression/elimination of the anti-Chlamydia abzyme activity and the trial results are shown up to up to 60 days after administration of placebo/therapy.

The titre of anti-Chlamydia antibodies was measured in the Therapy group using the method previously described (see Table 28). The severity of clinical symptoms was also measured (see Table 28)

Results of the monitoring of the suppression of the anti-Chlamydia abzyme activity are presented in the following tables (Tables 22-27).

At first it was noticed that in two weeks of the therapy in all groups there was a significant reduction in the abzyme activity. The most prominent was in the Therapy Group B where the use of a nonspecific inhibitor, azithromycin, was combined with use of a specific inhibitor, aspirin (Table 23). Indeed, the level of the activity in this group reached the level of clinically healthy individuals (see Summary Table 28). An important observation was that patient TGB7 in this group showed a large increase in abzyme level (which correlated with a worsening of clinical symptoms) on the $45^{th}$ day (double asterix—Table 23) and then after another 15 days of treatment the patient started to feel better and abzymes had reduced to 0. TGB7 also showed an increase in ApoB levels (asterix—see Table 7) at the same time as an increase in abzymes level at 45 days.

The least effective therapy was in the Therapy Group A (azithromycin only—Table 22) where for 27% of the patients (3 out of 11, marked with an asterix) there were no changes in the abzyme activity after 15 days. However, a continued reduction for the majority of the patients was reversed for two of them in the first group on the $30^{th}$ day of the trial (TGA2 and TGA6, Table 1, marked with two asterixes). This observation, together with the fact that there were some patients with, although reduced, a remaining significant level of the abzyme activity, led to the extension of treatment for another 30 days, resulting in significant decreases in all patients. In therapy group A clinical symptoms of patients TGA2 and TGA6 improved for 15 days and correlated with a reduction in the abzyme level, however clinical symptoms worsened and abzymes level increased around the $30^{th}$ day of the trial (double asterix—Table 22).

In Therapy Group C (Azithromycin and antioxidants) there was one patient (TGC1) who showed no decrease in abzyme activity (asterixed—Table 24)

The use of aspirin alone, in the prescribed dose, without azithromycin, led to a reduction in the abzyme activity but to a lesser degree than observed with the combination (Therapy Group D—Table 25).

The applied anti-abzyme therapy has significantly improved the clinical condition of the majority of the patients, which was evaluated with the modified Rose-Blackburn Questionnaire (Table 27) and verified by the use of the treadmill exercise/stress ESG testing. At the same time there was no positive clinical dynamic noticed in the control group, even for a single patient. In Table 27 PCG indicates Patient Control Group, $^§$ indicates results obtained by immuno-fluorescent assay, $^{§§}$ indicates results obtained by immuno-enzymatic assay, $^{§§§}$ indicates results obtained by immuno-turbidimetric assay. * indicates a statistically significant difference.

No statistically significant changes were observed for the following parameters of coagulation; Kaolin Clotting Time, activated Partial Thromboplastin Time, Prothrombin time. There were no changes registered in the level of the serum Creatinine and the liver enzymes Alanine aminotransferase and Aspartate aminotransferase.

No patients in the experimental therapy groups had had positive changes in their clinical conditions for a number of months/years prior to their selection for the trial. Therefore, this absence of positive dynamic can be used as the 'internal' control for the significant clinical progress of the patients which has been observed.

The original intensive regimen of abzyme inhibitor, which has anti-microbial properties, totally eliminated the presence of anti-Chlamydia IgG. This effect exceeds results of all previously undertaken trials with azithromycin—Gupta et al., ROXIS, ACADEMIC, STAMINA, WIZARD, where the best one showed a reduction of titers of these antibodies only in 43% of the treated patients (Gupte S., et al. Circulation (1997), 96, 404-407, Gurfinkel E., et. al. Lancet (1997), 350, 404-407, Cambell L. A. et al., In: Program and Abstracts of the $4^{th}$ International Conference on the Macrolides, Azalides, Streptogramins and Ketolides; January 21-23, (1998); Barcelona, Spain. Abstract 416, Anderson J. L. et al. Circulation (1999), 99, 1540-1547, Stone A. F. M. et. al. Paper presented at European Society of Cardiology XXIII Congress; September 1-5, (2001); Stockholm, Sweden, Komarov A. L. Heart—Russian (2002), v.1, N°3, 152)

By targeting the anti-Chlamydia abzymes, significant improvements in lipid concentrations and thrombosis were achieved (Table 27) Therefore, it is possible to suggest that the developing abnormalities in the lipid metabolism and coagulation system in atherosclerosis are secondary to the appearance of these lipid-oxidising catalytic antibodies.

The observed beneficial effect of azithromycin could not be explained by its anti-bacterial properties because only in 15 patients out of 30 (in 50%) selected for the trial had beforehand tested positive on the presence of Chlamydia infection. The level of anti-Chlamydia IgG in the serum of another 8 patients was insignificant, below 1:32 in immuno-fluorescent assay. The other 7 patients tested negative.

The diagnostic test indicates whether a patient carries abzymes and is not necessarily correlated with the patient being positive for Chlamydia IgG antibodies. Therefore, the therapy should not be prescribed on the basis of seropositivity for Chlamydia. This shows the usefulness in the invention when the diagnostic test is linked to administration of the correct therapy followed by repeated prognostic tests to monitor clearance of abzymes using the treatment.

Certain IHD patients in the theranostic trial were negative for anti-Chlamydia IgG antibodies but tested positive for abzymes. The abzyme and Rose-Blackburn Test scores before and after treatment for these patients are shown in shown in table 29. These patients were treated and their abzyme activity reduced with a subsequent improvement in clinical symptoms.

These results show that whether a patient carries abzymes is not necessarily correlated with the patient being positive for Chlamydia IgG antibodies. An atherosclerotic condition cannot be diagnosed or therapy prescribed on the basis of seropositivity for Chlamydia. However, abzymes are shown to be useful as a diagnostic marker of atherosclerotic conditions and may be linked to administration of the appropriate therapy followed by repeated prognostic tests to monitor clearance of abzymes.

EXAMPLE 14

Anti-Abzyme/Antioxidant Properties of Azithromycin

The inhibitory activity of Azithromycin on abzymes isolated from an atherosclerotic lesion was measured as described above. The results are shown in Table 30. Each number is a mean of duplicate/triplicate measurement, and calculated as a difference between the level of MDA accumulation in the tested serum before and after the addition of 0.5 of immunization dose of ovine Chlamydia vaccine ('Intervet'). The effect of DMSO was deducted from the readings where indicated (**).

Azithromycin was found to be a strong in vitro inhibitor of abzyme activity. This activity may be responsible for the in vivo biological effects observed with azithromycin, such as the rapid decrease in abzyme activity after administration of azithromycin.

EXAMPLE 15

Membrane Integrity of Chlamydia and Abzyme Activity

Abzyme activity was measured as described above using formalin, ammonium sulphate or SDS treated samples of *Chlamydia pneumoniae* or *Chlamydia Psittaci*. In these reactions, no lipid oxidising reaction in the test system.

Treatment of the Chlamydia bacteria with chaotropic agents, including non-ionic detergents 1% Triton X-100 and Igepal CA-630, 10% solution of DMSO, which preserve the presence of the membrane lipids in the system but disrupt the integrity of the bacterial membrane, completely abrogated the development of lipid oxidation reaction.

These experiments indicate that lipids are important for the initiation and the development of the reaction(s) of lipid peroxidation developing in the test system. In particular, a role for lipopolysaccaride, which is disrupted by the above treatmemts is indicated.

EXAMPLE 16

Case Histories

CASE No 1.

A 64 year old male patient was diagnosed with Ischaemic Heart Disease 3 years ago when he had the first symptoms of angina pectoris. The diagnosis was confirmed by coronary angiography, which established a stenosis of two arteries: 75% of the right coronary artery and 100% occlusion of the anterior intraventricular artery.

He was selected for the theranostic trial on the grounds that abzymes were detected in his serum. A combination of two abzyme inhibitors, azithromycin, in the dose of 500 mg daily, and aspirin, in the dose of 250 mg daily. His level of anti-Chlamydia IgG was high with a titer of 1:256.

Before the treatment his clinical condition, estimated by a score of a modified Rose-Blackburn protocol, was 19. The abzyme activity was 25 µM MDA/ml, the level of total cholesterol 226 mg/dL, triglycerides—90 mg/dL, HDL-cholesterol—56 mg/dL, LDL-cholesterol—73 mg/dL, ApoA—139 mg/dL, ApoB—81 mg/dL, alanine aminotransferase (ALT)—25 U/L, aspartate aminotransferase (AST)—29 U/L, creatinine—0.71 mg/dL.

During the treatment there were no significant adverse reactions noticed. On his first visit after the start of the therapy, 15 days, he reported a certain improvement in the signs of his disease. This improvement continued until the $30^{th}$ day of the therapy This was supported by an increase in the tolerance time during treadmill exercise ESG testing by modified Bruce Protocol.

At that time neither the abzyme activity nor the presence of anti-Chlamydia IgG was detected in his serum. The level of lipid parameters also improved: total cholesterol reduced to 172 mg/dL, triglycerides to—80 mg/dL, HDL-cholesterol—52 mg/dL, LDL-cholesterol—64 mg/dL, ApoA—110 mg/dL, ApoB—67 mg/dL. The level of ALT, AST and creatinine remained the same—25 U/ml, 27 U/ml and 0.7 mg/dL respectively.

On the arrival of the $45^{th}$ day from the beginning of the therapy he reported that a week before, on the $38^{th}$ day from the beginning, his condition had started to deteriorate—the frequency and intensity of the angina attacks had suddenly increased. This coincided with a rise in abzyme activity, which reached 80 µM MDA/ml. However, it is important to note, no 'traditional' anti-Chlamydia IgG were registered.

At the same time, the parameters of the lipid metabolism also deteriorated: total cholesterol increased to 185 mg/dL, triglycerides—143 mg/dL, LDL-cholesterol—74 mg/dL, ApoA—115 mg/dL, ApoB—87 mg/dL. Level HDL-cholesterol and ApoA remained essentially the same—50 mg/dL and 115 mg/dL, correspondingly. An important observation was that the level of liver enzymes also changed, ALT increased to 35 U/L and AST to 39 U/L; creatinine concentration was 0.8 mg/dL.

However, continued therapy seemed to completely suppress/eliminate the abzyme activity, which was also accompanied by an improvement in the concentration of some lipid parameters: total cholesterol was reduced to 165 mg/dL, triglycerides to—100 mg/dL, mg/dL. Concentration of HDL-cholesterol was 47 mg/dL. LDL-cholesterol—72 mg/dL, ApoA—112 mg/dL. The level of ALT, AST and creatinine became 24 U/ml, 25 U/ml and 0.7 mg/dL respectively.

At the same time the ApoB level remained on the pre-treatment level 80 mg/dL. The initially improved clinical condition also returned to the level that it was before the beginning of the therapy, the Rose-Blackburn score was 19. To stabilize the suppressed level of the abzymes with an attempt to improve the clinical parameters of the patient, it was recommended to continue the prescribed anti-abzyme therapy.

No anti-Chlamydia IgG was detected in this patient from the $15^{th}$ day of the start of the therapy onwards and the continued use of azithromycin was aimed at controlling the suppressed level of the cross-reacting abzymes, which bind and oxidise lipoproteins, rather than bacterial infection per se.

CASE No.2

A 46 year old male patient was diagnosed with IHD when he was admitted with an acute myocardial infarction on Feb. 21 2002. Before that he had no history of heart disease. The following May a coronary angiography revealed no stenosis/narrowing of his coronary arteries.

This patient was selected for a theranostic trial on the grounds that significant activity of the anti-Chlamydia abzymes was detected in his serum. It was 140 µM MDA/ml. A combination of two types of abzyme inhibitors, azithromycin, in the dose of 500 mg daily, and an antioxidant cocktail of vitamins E, A, C, was prescribed. The daily dose of vitamin E was 30 mg, vitamin A 1,500 EU and vitamin C 90 mg.

There was no detectable level of 'traditional' anti-Chlamydia IgA, IgG or IgM detected in the serum of this patient before or during the treatment period. Before the treatment his clinical condition, estimated by the score of a modified Rose-Blackburn protocol, was 17. The level of total cholesterol was 205 mg/dL, triglycerides—129 mg/dL, HDL-cholesterol—39 mg/dL, LDL-cholesterol—80 mg/db, ApoA—152 mg/dL, ApoB—221 mg/dL.

During treatment no significant adverse reactions were noticed. He started to feel a certain improvement in signs of the disease after the first two weeks of the treatment. This progress continued through the whole period of the therapy of 60 days. This was supported by a significant increase in the tolerance time during treadmill exercise ESG testing carried out in accordance with modified Bruce Protocol.

At the end of the observation period, after 60 days, neither the abzyme activity nor the presence of anti-Chlamydia IgG was detected in his serum.

These changes in abzyme activity coincided with a significant improvement in the clinical condition of the patient. His score on the modified Rose-Blackburn protocol reduced from 17 before the treatment to 13 after it.

EXAMPLE 17

Effect of Anti-Abzyme Therapy on Thrombosis

One of the indicators of atherosclerotic disorders is that patients often present with aberrations in the time it takes for their blood to form clots (this is generally increased in patients). A number of pathways can lead to clot formation and therefore there are four internationally recognized tests for clotting time. The first is called Activated Partial Thromboplastin Time (APTT) and works by adding thromboplastin and calcium to measure the intrinsic pathway. The second called Prothombin Time (PT) is a simple measurement for the extrinsic pathway. Silica clotting time (SCT) measures clotting induced by fine particles (silica) and Kaolin Clotting Time (KCT) measures clotting induced by larger particles (Kaolin). For all these fast clotting times are indicative of higher risk of thrombosis.

Before treatment, the clotting times using all four methods for all patients in all therapy groups were measured and the mean calculated with a standard error. Measurements were repeated 60 days later. Controls were our Patient Control Group (measurements taken once—values did not change significantly for these patients over time) and also form our clinically healthy control group. The results of treatment are shown in Table 32.

The average value for patients before treatment for the APTT test was 22.4±0.89 (comparable with the Patient Control Group value of 25.2±1.37) and was significantly different from the clinically healthy group value of 49.1+7. After treatment the patients had a mean value of 46.9±6.45 and was therefore within the 'normal range' of clotting times i.e. had been normalized.

The average value for patients before treatment for the PT test was 13.5±0.94 (comparable with the Patient Control Group value of 17.3±4.05) and lower than the clinically healthy group value of 23.7±4.01. After treatment the patients had a mean value of 25.3±4.05 and was therefore within the 'normal range' of clotting times i.e. had been normalized.

The average value for patients before treatment for the SCT test was 151±15.0 (comparable with the Patient Control Group value of 137±11.5) and significantly lower than the clinically healthy group value of 248±10.0. After treatment the patients had a mean value of 235±17.9 and was therefore within the 'normal range' of clotting times i.e. had been normalized.

The average value for patients before treatment for the KCT test was 51.2±4.59 (comparable with the Patient Control Group value of 50.3±2.16) and was significantly different from the clinically healthy group mean value of 133±23.7. After treatment the patients had a mean value of 126±34.2 and was therefore within the 'normal range' of clotting times i.e. had been normalized.

These results show that anti-abzyme therapy can be used to normalize clotting times (using all Internationally recognized clotting time assays) and reduce the risk of thrombosis and hence heart attack and stroke.

Figure 14:
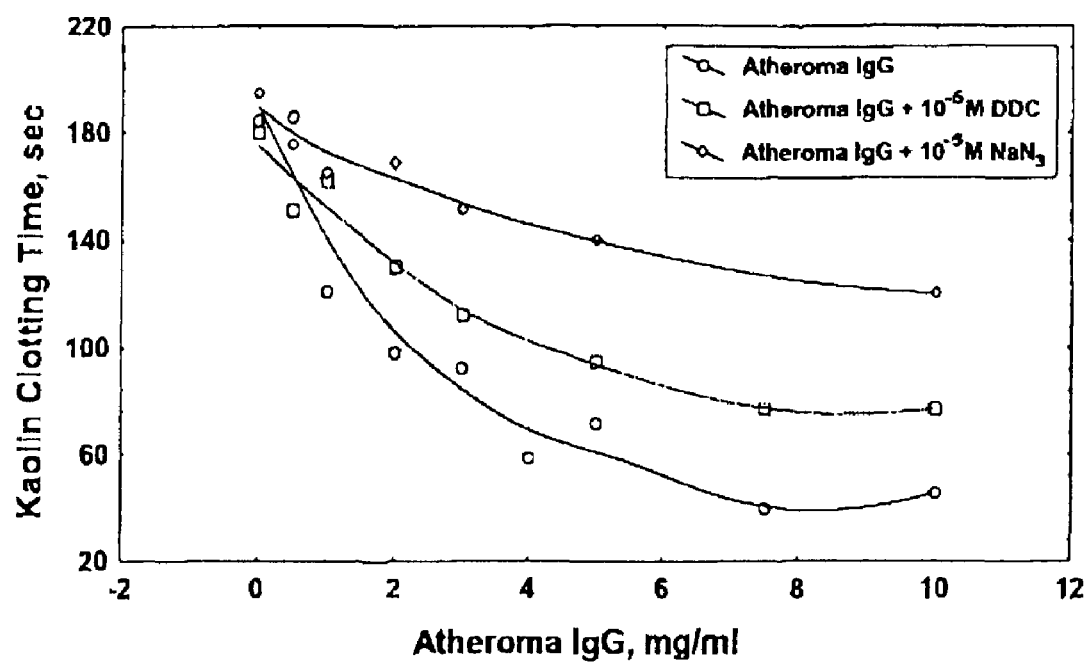
FIG. 14 shows the effect of anti-Chlamydia abzymes on Kaolin Clotting Time. Abzymes were inhibited by their pre-incubation with sodium azide ($NaN_3$) or diethyldithiocarbamate (DDC); pH of the tested plasma was 6.2.

The results of in vitro experiments shown in FIG. 14 indicate that addition of the fraction of atheroma IgG containing anti-Chlamydia abzymes, in concentration from 0.5 to 10 mg of protein, had an activated effect on the kaolin clotting of the tested plasma.

Pre-incubation of the abzymes either with diethyldithiocarbamate or sodium azide, which inhibit these antibodies via binding to $Cu^{2+}$ in their active centre, led to a reduction of the abzyme effect on the plasma clotting.

These data indicate that the anti-Chlamydia abzymes can directly interfere with the thrombosis of human plasma, and are an important factor in the development of Ischaemic Heart Disease.

TABLE 1

| IgG from human atherosclerotic lesion, in µg | Lipid peroxidation, in µM MDA per ml | |
|---|---|---|
| | +10 µl ovine Chlamydia | +2.5 µl feline Chlamydia |
| 0 (control) | 3 ± 0.4 | 0 ± 0.3 |
| 0.18 | 6 ± 1.1 | 2 ± 0.7 |
| 0.36 | 2 ± 1.2 | 0 ± 0.5 |
| 0.57 | 10 ± 0.9 | 1 ± 0.2 |
| 0.8 | 18 ± 1.0 | 0 ± 0.4 |
| 1.35 | 19 ± 0.7 | 0 ± 0.5 |
| 1.8 | 26 ± 1.3 | 0 ± 0.8 |
| 5.4 | | 4 ± 0.3 |
| 8.0 | | 23 ± 1.5 |

TABLE 2

| Tested systems | Lipid peroxidation in serum, in µM MDA/ml | |
|---|---|---|
| | without Chlamydia | +10 µl ovine Chlamydia |
| Lipoproteins + antibodies (1st control) | | |
| Serum lipoproteins | 130 ± 9.43 | 193 ± 19.9 |
| +1 µg/ml of lesion IgG* | 246 ± 17.5 | 342 ± 8.52 |
| Only antibodies (2nd control) | | |
| Lipoprotein removed from serum by ultracentrifugation +1 µg/ml lesion IgG* Removal of antibodies by pre-absorption with serum lipoproteins | 29 ± 3.57 | 63 ± 5.42 |
| Serum was initially incubated with 1 µg/ml of lesion IgG* and then lipoproteins were removed by ultracentrifugation | 35 ± 4.66 | 23 ± 1.71 |

TABLE 3

| Serum | Control serum, MDA in µM/ml | Patient No3' serum, MDA in µM/ml |
|---|---|---|
| Initial level | 58 ± 4.5 | 187 ± 5.0 (100%) |
| +6.25 µl feline Chlamydia | 50 ± 2.8 | 225 ± 9.9 (120%) $p < 0.05$ |

TABLE 6

| LDL, 480 µg of protein | Level of MDA production by 0.82 µg of lesion IgG, in µM |
|---|---|
| Control | 0.49 ± 0.023 |
| +0.1 M sodium formate | 0 |
| +0.1 mM ascorbic acid* | 0 |
| +0.1 M benzole acid | 0 |
| +1% DMSO* | 0 |

*Antioxidants approved by for use in humans in most developed countries.

TABLE 4

| | Control' serum, MDA in µM/ml | | | Patient No2' serum, MDA in µM/ml | | |
|---|---|---|---|---|---|---|
| | Initial | +ovine Chlamydia | | Initial | +ovine Chlamydia | |
| Samples | level | 10 µl | 100 µl | level | 10 µl | 100 µl |
| Serum | 56 ± 6.4 | 58 ± 5.0 | 48 ± 6.6 | 128 ± 9.0 (100%) | 202 ± 13.4 (158%) $p < 0.01$ | 580 ± 24.2 (453%) $p < 0.001$ |
| Serum-IgG | 52 ± 6.2 | 60 ± 6.6 | 62 ± 7.2 | 76 ± 4.4 | 72 ± 6.8 | 96 ± 8.4 |

TABLE 5

| | Lipid peroxidation in µM MDA per 1 ml of serum | | |
|---|---|---|---|
| Cases | Before the addition of Chlamydia* | After the addition of Chlamydia* | Increment |
| Control: K | 58 | 90 | 32 |
| K1 | 104 | 124 | 20 |
| K2 | 124 | 148 | 24 |
| K3 | 131 | 168 | 37 |
| K4 | 106 | 124 | 18 |
| M | 112 | 108 | −4/0 |
| M1 | 70 | 70 | 0 |
| M2 | 78 | 86 | 8 |
| M3 | 102 | 80 | −22/0 |
| M4 | 84 | 76 | −8/0 |
| | 1/10 or 10% | 1/10 or 10% | 13.9 ± 5.14 (n = 10) |
| | 96.8 ± 3.99 (n = 10) | 108 ± 5.73 (n = 10) $p_{(*Chlamydia)} > 0.05$ | |
| Patients: 1 | 116 | 166 | 50 |
| 4 | 86 | 106 | 20 |
| 5 | 122 | 168 | 46 |
| 6 | 40 | 62 | 22 |
| 6a | 208 | 336 | 128 |
| 7 | 118 | 166 | 48 |
| 8 | 82 | 98 | 16 |
| 9 | 160 | 290 | 130 |
| 10 | 60 | 80 | 20 |
| 11 | 236 | 368 | 132 |
| 12 | 256 | 328 | 72 |
| 13 | 174 | 350 | 176 |
| 14 | 168 | 306 | 138 |
| 15 | 126 | 162 | 36 |
| 16 | 290 | 290 | 0 |
| 17 | 246 | 342 | 96 |
| 18 | 270 | 376 | 106 |
| 19 | 156 | 272 | 116 |
| 20 | 164 | 312 | 148 |
| 21 | 206 | 344 | 138 |
| 22 | 290 | 332 | 42 |
| | 13/21 or 62% | 17/21 or 81% | 80.0 ± 13.1 (n = 21) $p_{(control)} < 0.001$ |
| | 170 ± 10.8 (n = 21) $p_{(control)} < 0.001$ | 250 ± 15.0 (n = 21) $p_{(control)} < 0.001$ $p_{(*Chlamydia)} < 0.01$ | |

TABLE 7

| Metals | Chelators | Proprietary Preparations |
|---|---|---|
| $Fe^{+2}/Fe^{+3}$ | Desferri-oxamine Mesylate | Canad.: Zinecard, Fr.: Cardioxane; Ital.: Cardioxane; Eucardion; USA: Zinecard |
| | Haem Derivatives | Austral.; Pannematin, Fr.: Normosang; USA: Panhematin |
| $Cu^{+1}/Cu^{+2}$ | Penicillamine | Aust.: Artamin; Distamine, Austral.: D-Penamine, Belg.: Kelatin, Canad.: Cuprimine; Depen; Fr.: Trolovol; Ger.: Metacaptase, Trisorcin, Trolovol; Irl.: Distamine; Ital.: Pemine; Sufortan; Neth.: Cuprimine, Distamine; Gerodyl; Kelatin; Norw. : Cuprimine; S.Afr.: Metaalcaptase; Spain: Cuprein; Sufortanon; Swed.: Cuprimine; Switz.: Mercaptyl; UK: Distamine, Pendramine; USA: Cuprimine, Depen. |
| | Tiopronin | Fr.: Acadione; Ger.: Captimer, Ital.: Epatiol, Mucolysin; Mucosyt; Thiola; Tioglis; Spain: Sutilan; Switz.: Mucolysin; USA: Thiola. Multi-ingredient: Ital.: Mucolysin Antibiotico; Spain: Hepadigest. |
| | Trientine Dihydrochloride | USA: Syprine. |
| | Diethyldithio-carbamate | |
| | Acetylsalicylic acid | |
| $Me^{+2}$* | Disodium/Trisodium Edetate | Fr.: Chelatran; Tracemate; Irl.: Limclair; UK: Limclair, USA: Disotate; Endrate Multi-ingredient; Canad.: Murine Supplement Tears; Fr.: Vitaclair; Ger.: Complete, Duracare; Oxysept; UK: Uriflex G; Uriflex R. |
| | Edetic Acid | Multi-ingredient: Ital.: Conta-Lens Wetting; USA: Summer' sEve Post-Menstrual, Triv, Vagisec Plus; Zonite |
| | Unithiol | Ger.: Dimaval; Mercuval. |
| Other metals of transient valence | | |

*Any bivalent metal

TABLE 8

| Antibacterial agents | Proprietary Preparations |
|---|---|
| Tetracycline | Aust: Achromycin; Actisite; Hostacyclin, Latycin, Steclin; tetrarco; Austral.: Achromycin; Achromycin V, Latycin, Mysteclin; Panmycin P; Steclin-V; Tetramykoin; Tetrex; Belg.: Hostacucline, Canad.: Achromycin; Achromycin V; Apo-Tetra; Novo-Tetra; Nu-Tetra, Tetracyn; Fr.: Florocycline, Hexacycline, Tetramig; Ger.: Achromycin; Akne-Pyodron Kur; Akne-Pyodron oral, Dispatetrin; Hostacyclin; Imex; Quimocyclin N; Sagittacin N, Steclin; Supramycin; Tefilin; Tetrabakat; Tetrablet; Tetracitro S; Tetralution; Ital.: Acromicina; Ambramicina; Calociclina; Ibicyn; Spaciclina; Tetra-Proter; Tetrabioptal; Tetrafosammina, Neth.: Tetrarco; S.Afr.: Achromycin; Arcanacycline; Gammatet; Hostacycline; Rotet; Tetrex; Spain: Actisite, Ambramicia, Britaciclina; Kinciclina; Quimpe Antibiotico; Tetra Hubber, Tecralen; Tetrarco Simple; Swed.: Achromycin; Actisite; Switz.: Achromycine; Actisite, Servitet; Tetraseptine; Triphacycline; UK: Achromycin; Economycin; Sustamycin. Tetrabid-Organon; Tetrachel; USA: Achromycin V; Achromycin; Actisite, Nor-Tet, Panmycin; Robitet Robicaps; Sumycin; Teline; Tetracap; Tetralan, Tetram.* |
| Erythromycin | |
| Azithromycin | |
| Roxithromycin | |
| Ofloxacin | |
| Clinafloxacin | |
| Ciprofloxacin | |
| Clindamycin | |
| Doxycycline | |
| Minocycline | |

*Multi-ingredient. numerous preparations

TABLE 9

| Antioxidants | Proprietary Preparations: |
|---|---|
| Alpha-Tocopherol | Aust.: Avigilen; Ephynal; Etocovit; Evit, Evitol, Tetefit Vitamin E, Austral: Alpha Keri Silky Smooth; Bioglan Micelle E; Bioglan Natural E; Bioglan Water Soluble E; Chew-E; Dal-E; Invite E Forte, Invite E, Marco E; Mega E; Megavit Natural E, Belg.: Ephynal, Canad.: Aquasol E; Novo E; Organex; Vita-E; Fr.: Ephynal; Tocalfa; Toco; Tocomine, Ger.: Antioxidants E; Biopto-E; Detulin; E-Muslin; E-Vicotrat, Ecoro; Embial; Ephynal; Pexan E; Puncto E; Sanavitan S; Tocorell, Tocovenos, Tocovital; Togasan; Vitagutt Vitamin E; Irl.: Ephynal; Ital.: E Perle; E-Vit; E-Vitum; Ephynal; Evasen Cream, Evion; Evitina; Fertilvit; Na-To-Caps; Tocoferina E; Tocoferolo Bioglan, Tocogen; Viteril; Norw.: AFI-E; Ido-E; S. Afr.: Ephynal; Spain: Auxina E, Ephynal; Glutaneurina B6 Fte; Swed.: Ephynal; Opto Vit-E; Vitacim, UK: Bio E, Ephynal; Praire Gold; Vita-E; USA: Amino-Opti-E; Aquasol E; Aquavit-E, Vita-Plus E; Vitec* |
| Mannitol | Aust.: Osmofundin 20%, Austral.: Mede-Prep; Osmitrol; Canad.: Osmitrol, Fr.: Manicol; Ger.: Eufusol M 20; Mannit-Losung; Osmoofundin 15%; Osmosteril 20%; Thomaemannit; Ital.: Isotol, Mannistol; Switz.: Mannite; USA: Osmitrol; Resectisol.* |
| Silidianin | Aust.: Apihepar.; Biogelat leberachutz, Hepar Pasc Mono; Legalon; Silyhexal; Austral.: Herbal Liver Formula; Liver Tonic Capsules, Prol.; Belg.: Legalon SIL; Fr.: Legalon; Ger.: Alepa; Ardeyhepan N, Carduus-monoplant; Cefasliymarin, Divinal-Hepa, Durasilymarin; Hegrimarin; Heliplant; Hepa-loges N; Hepa-Merz Sil; Hepar-Pasc; Heparano N; Heparsyx N; Hepatorell; Hepatos; Heplant, Legalon; Legalon SIL, Logomed Leber-Kapseln; Mariendistel Curarina; Phytohepar; Poikicholan; Probiophyt V, Silibene, Silicur, Silimarit, Silmar; Sulfolitruw H., Vit-o-Mar; Ital: Eparsil, Legalon, Locasil; Marsil; Silepar; Silimarin, Silirex, Silliver; Silmar; Trissil, S.Afr.: Legalon, Spain: Legalon; Silarine; Silimazu; Switz.: Legalon; Legalon SIL. |
| Ascorbic acid | |
| Etc. | |

*Multi-ingredient: numerous preparations

TABLE 10

Lipid peroxidation of sheep sera in μM MDA per ml

| Sheep | −Chlamydia | +Chlamydia |
|---|---|---|
| Pre-vaccinated | | |
| No. 1 | 44 | 39 (89%) |
| No. 2 | 59 | 67 (114%) |
| Post-vaccinated | | |
| No. 8 | 67 | 85 (127%) |
| No. 5 | 54 | 46 (85%) |
| Post-abortion (wild type) | | |
| A | 48 | 102 (212%) |
| B | 63 | 118 (187%) |

TABLE 11

| $Me^{2+}$-binding agent, 10 μM of each | Lipid oxidising activity of anti-Chlamydia abzymes in, μM MDA/ml* | Result | Potential clinical use of agent for inhibition of anti-Chlamydia abzymes |
|---|---|---|---|
| Control | 24.3 | | |
| $NaN_1$ | 0 | Positive | Highly toxic, no use |
| KCN | 0 | Positive | Highly toxic, no use |
| Tetracycline | 18.3 | Negative | No use |
| DTPA | 45.2 | Negative | No use |
| Picolinic acid | 0 | Positive | Prooxidant, no use |
| $Cu^{2+}$-chelators | | | |
| DDC | 0 | Positive | Possible use ("Imutiol") |
| Acetylsalicylic acid | 6.2 | Positive | Possible use ("Aspirin") |
| Penicillamine | 0 | Positive | Possible use ("Penicillamine") |

*Each number is a mean of duplicate/triplicate measurement, and calculated as a difference between the level of MDA accumulation in the tested serum before and after the addition of 0.5 of immunisation dose of ovine Chlamydia vaccine ('Intervet').

TABLE 12

| Inhibitor | Mechanism of action | In-vitro Inhibition (+ = inhibition) (− = no inhibition) |
|---|---|---|
| Tetracycline | Fe2+ inhibition | − |
| DDC | Free and bound Cu2+ inhibition | + |
| Aspirin (acetylsalicylic acid) | Free and bound Cu2+ inhibition | + |
| Penicillamine | Free and bound Cu2+ inhibition | + |
| CN— | Free and bound Metal inhibition | + |
| N3 | Free and bound Metal inhibition | + |
| DTPA | Free metal inhibition only | − |
| Picolinic acid | Free and bound Metal inhibition | + |

TABLE 13

Level of activity of anti-Chlamydia abzymes in μM MDA/ml

| Initial of patient with CHD | Before taking aspirin | 7 days after starting to take 250 mg of aspirin daily |
|---|---|---|
| S | 45 | 0 |
| A | 100 | 20 |
| Y | 45 | 0 |

TABLE 14

Level of activity of anti-Chlamydia abzymes in μM MDA/ml

| Initial of patient | Aspirin intake 250 mg daily | After stopping taking aspirin for 7 days | 7 days after re-starting to take 250 mg aspirin daily |
|---|---|---|---|
| F | 10 | 65 | 20 |

TABLE 15

Anti-Chlamydia abzyme activity, in μM MDA/ml

| Patient | before treatment | 15 days after the start of the treatment | 30 days after the start of the treatmnet |
|---|---|---|---|
| 1. | 30 | 6.7 | 3.3 |
| 2. | 90 | 6.7 | — |
| 3. | 80 | 0 | 0 |
| 4. | 40 | 60 | 37 |
| 5. | 50 | 0 | 0 |
| 6. | 15 | 8.3 | 28 |
| 7. | 10 | 6.7 | 3.3 |
| 8. | 35 | 33 | 10 |
| 9. | 85 | 75 | 78 |
| 10. | 30 | 0 | 0 |
| 11. | 40 | — | — |
| | 45.9 | 19.6 | 17.7 |

TABLE 16

Anti-Chlamydia abzyme activity, in μM MDA/ml

| Patient | before treatment | 15 days after the start of the treatment |
|---|---|---|
| 12 | 100 | 43 |
| 13 | 93 | 27 |
| 14 | 33 | 0 |
| 15 | 30 | 0 |
| 16 | 153 | 0 |
| 17 | 15 | 0 |
| 18 | 25 | 3.3 |
| 19 | 15 | 0 |
| | 58.0 | 9.16 |

TABLE 17

| Patient | Clinical condition | |
|---|---|---|
| | Before treatment | After 15 days of treatment |
| 2 | Unstable angina; ECG exercise test was inapplicable | Stable condition; ECG exercise test demonstrated a significant tolerance; angina attacks were not recorded for this period; return to his job in full capacity |
| 5 | Classified as angina class III; 10 tablets of nitroglycerine daily | Based on the improvement of ECG exercise test, patient condition was reclassified as angina class II; reduction in the frequency and severity of angina attacks; 5 tablets of nitroglycerine daily; |

TABLE 18

| CONTROL | SILENT ISCHAEMIA | STABLE ANGINA | UNSTABLE ANGINA | MYOCARDIAL INFARCTION | |
|---|---|---|---|---|---|
| | | | | Acute Phase 1st-3rd Day | 14th Day |
| $6.36 \pm 1.14$ (n = 67) 11/67 = 16% | $68.8 \pm 16.7$ (n = 15) 14/15 = 93% $P_{control} < 0.001$ | $37.1 \pm 2.23$ (n = 193) 130/193 = 67% $P_{control} < 0.001$ | $101 \pm 18.1$ (n = 13) 12/13 = 92% $P_{control} < 0.001$ $P_{stable\ angina} < 0.001$ | $14.4 \pm 2.60$ (n = 25) 12/25 = 48% $P_{control} < 0.01$ $P_{unstable\ angina} < 0.001$ | $80.6 \pm 21.4$ (n = 14) 12/14 = 86% $P_{acute\ phase} < 0.01$ |

TABLE 19

ISCHAEMIC HEART DISEASE (total): 168/235 = 71%

| STABLE ANGINA | | | | | | UNSTABLE ANGINA | |
|---|---|---|---|---|---|---|---|
| I | | II | | III | | IV | |
| | + aspirin | | + aspirin | | + aspirin | | + aspirin |
| 15 | 0 | 45 | 30 | 45 | 20 | 70 | 180 |
| 75 | 5 | 0 | 5 | 40 | 0 | 90 | 130 |
| 15 | 45 | 70 | 10 | 10 | 45 | 30 | 70 |
| 15 | 0 | 50 | 10 | 45 | 0 | 250 | 0 |
| | 10 | 20 | 0 | 60 | 5 | 140 | 37 |
| | 0 | 0 | 5 | 90 | 35 | 130 | 90 |
| | | 8 | 25 | 25 | 0 | | 100 |
| | | 0 | 0 | 30 | 15 | | |
| | | 53 | 5 | 153 | 30 | | |
| | | 18 | 22.5 | 15 | 105 | | |
| | | 17 | 0 | 93.3 | | | |
| | | 43 | 5 | | | | |
| | | 10 | 3.3 | | | | |
| | | 50 | 0 | | | | |
| | | 32.5 | 16.7 | | | | |
| | | 100 | | | | | |
| | 1/6 | | 4/15 | | 6/10 | | 6/7 |
| | 17% | | 27% | | 60% | | 86% |
| 30.0 (n = 4) | 10.0 (n = 6) | 32.2 (n = 16) | 9.2 (n = 15) | 56.0 (n = 11) | 25.5 (n = 10) | 119 (n = 6) | 86.7 (n = 7) |
| 4/9 = 44% | | 12/26 = 46% | | 12/17 = 71% | | 12/13 = 92% | |

TABLE 20

| Rabbit | Anti-Chlamydia IgG, ELISA** Day of the infection | | Anti-Chlamydia abzymes, in µM MDA/ml** Day of the infection | |
|---|---|---|---|---|
| | 0 | 14 | 0 | 14 |
| 1 | 0 | 1:1,600 | 0 | 71 |
| 2 | 0 | 1:3,200 | — | 203 |
| 3 | 0 | 1:800 | 0 | 131 |
| Control | 0 | 0 | 0 | 0 |

TABLE 21

| Rabbit | Anti-Chlamydia IgG, ELISA** Day of the infection | | | Anti-Chlamydia abzymes, in µM MDA/ml** Day of the infection | | |
|---|---|---|---|---|---|---|
| | 0 | 14 | 22 § + vaccine | 0 | 14 | 22 § + vaccine |
| 1 | 0 | 1:1,600 | 1:1,600 | — | 0 | 71 | 165 | — |
| 2 | 0 | 1. | 1:3,200 | — | — | 203 | 180 | — |
| 3 | 0 | 3,200 1.600 | — | 1:1,600 | 0 | 131 | — | 64 |
| Control | 0 | 0 | — | — | 0 | 0 | — | — |

TABLE 22

| Patients in Therapy Group A | Anti-Chlamydia abzyme activity, in µM MDA/ml | | | | |
|---|---|---|---|---|---|
| | before treatment | 15 days after the start of treatment | 30 days after the start of treatment | 45 days after the start of treatment | 60 days after the start of treatment |
| TGA1 | 30 | 6.7 | 3.3 | 0 | 0 |
| TGA2 | 90 | 6.7 | 78** | 17 | 3.3 |
| TGA3 | 80 | 0 | 0 | 0 | 6.7 |
| TGA4 | 40 | 60* | 37* | 0 | 0 |
| TGA5 | 50 | 0 | 0 | 20* | 0 |
| TGA6 | 15 | 8.3 | 28** | 43* | 6.7 |
| TGA7 | 28 | 6.7 | 3.3 | 3.3 | 0 |
| TGA8 | 35 | 33 | 10 | 3.3 | 0.5 |
| TGA9 | 85 | 75* | 78* | 0 | 0 |
| TGA10 | 30 | 0 | 0 | 5.0 | 0 |

TABLE 22-continued

Anti-Chlamydia abzyme activity, in μM MDA/ml

| Patients in Therapy Group A | before treatment | 15 days after the start of treatment | 30 days after the start of treatment | 45 days after the start of treatment | 60 days after the start of treatment |
|---|---|---|---|---|---|
| TGA11 | 40 | 52* | 10 | 0 | 0 |
|  | 47.5 | 22.5 | 22.5 | 7.4 | 1.6 |

TABLE 23

Anti-Chlamydia abzyme activity, in μM MDA/ml

| Patients in Therapy Group B | before treatment | 15 days after the start of treatment | 30 days after the start of treatment | 45 days after the start of treatment | 60 days after the start of treatment |
|---|---|---|---|---|---|
| TGB1 | 100 | 43 | 10 | 0 | — |
| TGB2 | 93 | 27 | 30 | 0 | 10 |
| TGB3 | 33 | 0 | 0 | 0 | 0 |
| TGB4 | 30 | 0 | 6.7 | 0 | 3.3 |
| TGB5 | 153 | 0 | 0 | 0 | 3.3 |
| TGB6 | 15 | 0 | 0 | 3.3 | 0 |
| TGB7 | 25 | 3.3 | 0 | 80** | 0 |
| TGB8 | 15 | 0 | 3.3 | 10 | 0 |
|  | 58.0 | 9.16 | 6.25 | 11.6 | 2.4 |

TABLE 24

Anti-Chlamydia abzyme activity, in μM MDA/ml

| Patients in Therapy Group C | before treatment | 15 days after the start of treatment | 30 days after the start of treatment | 45 days after the start of treatment |
|---|---|---|---|---|
| TGC1 | 15 | 28* | 23* | 23* |
| TGC2 | 23 | 0 | 0 | 0 |
| TGC3 | 25 | 17 | 0 | 13 |
| TGC4 | 60 | 0 | 0 | 0 |
| TGC5 | 45 | 1.7 | 0 | 0 |
| TGC6 | 43 | 18 | 0 | 0 |
| TGC7 | 140 | 53 | 20 | 20 |
| TGC8 | 130 | 57 | 17 | 3.3 |

TABLE 24-continued

Anti-Chlamydia abzyme activity, in μM MDA/ml

| Patients in Therapy Group C | before treatment | 15 days after the start of treatment | 30 days after the start of treatment | 45 days after the start of treatment |
|---|---|---|---|---|
| TGC9 | 18 | 0 | 0 | 13 |
|  | 55.6 | 19.4 | 6.67 | 8.10 |

TABLE 25

| Patients in Therapy Group D | Anti-Chlamydia abzyme activity, in μM MDA/ml | |
|---|---|---|
|  | before treatment | 60 days after the start of treatment |
| TGD1 | 103 | 63 |
| TGD2 | 253 | 103 |
|  | 178 | 83.2 |

TABLE 26

| Patient Control Group (PCG) | Anti-Chlamydia abzyme activity, in μM MDA/ml | |
|---|---|---|
|  | At Day 1 | At Day 60 |
| PCG1 | 43 | 43 |
| PCG2 | 93 | 70 |
| PCG3 | 60 | 53 |
| PCG4 | 17 | 25 |
| PCG5 | 70 | 55 |
| PCG6 | 25 | 23 |
| PCG7 | 20 | 34 |
| PCG8 | 70 | 68 |
| PCG9 | 20 | 20 |
| PCG10 | 30 | 27 |
| PCG11 | 20 | 45 |
| PCG12 | 170 | 150 |
| PCG13 | 70 | 103 |
| PCG14 | 45 | 57 |
| PCG15 | 50 | 55 |
| PCG16 | 53 | 71 |
| PCG17 | 18 | 45 |
| PCG18 | 15 | 34 |
| PCG19 | 45 | 67 |
| PCG20 | 60 | 61 |
|  | 50.0 ± 7.08 | 55.3 ± 6.18 |

TABLE 27

| Parameter | | Azithromycin Therapy Group A | Azithromycin + antioxidants Therapy Group C | Azithromycin + aspirin Therapy Group B | PCG | Norm |
|---|---|---|---|---|---|---|
| Anti-Chlamydia abzymes activity, in μM/MDA/ml | Before treatment | 47.5 ± 8.96 | 55.0 ± 16.2 | 58.0 ± 20.4 | 50.0 ± 7.08 | 6.36 ± 1.14 |
|  | 60 days after treatment | 1.6 ± 0.89 $p < 0.001$* | 8.1 ± 3.60 $p < 0.05$* | 2.4 ± 1.37 $p < 0.05$* | 55.3 ± 6.18 $p > 0.05$ |  |
| Anti-Chlamydia IqG[3], (titers)$^{-1}$ | Before treatment | 43.6 | 48.5 | 52.0 | — | 0 |
|  | 60 days after treatment | 0 $p < 0.001$* | 0 $p < 0.001$* | 0 $p < 0.001$* | — | 0 |
| Clinical Status modified Rose | Before treatment | 19.4 ± 1.79 | 18.6 ± 0.81 | 20.4 ± 1.79 | 19.8 ± 1.43 | 0 |
|  | 60 days | 14.4 ± 1.14 | 15.4 ± 1.75 | 15.0 ± 1.17 | 21.5 ± 1.19 |  |

TABLE 27-continued

| Parameter | | Azithromycin Therapy Group A | Azithromycin + antioxidants Therapy Group C | Azithromycin + aspirin Therapy Group B | PCG | Norm |
|---|---|---|---|---|---|---|
| G., Blackburn H Questionnaire | after treatment | p < 0.05* | p > 0.05 | p < 0.01* | | |
| Coagulation Silica Clotting Time**, in sec | Before treatment | | 151 ± 18.8 | | | 200-250 |
| | 60 days after treatment | | 222 ± 18.4 p < 0.05* | | | |

| Therapy Group/Patient | Score by modified Rose-Blackburn Questionnaire | |
|---|---|---|
| | Before treatment | 60 days after start of the treatment |
| Therapy Group A | | |
| TGA1 | 25 | 17 |
| TGA2 | 22 | 19 |
| TGA3 | 12 | 10 |
| TGA4 | 19 | 13 |
| TGA5 | 23 | 16 |
| TGA6 | 21 | 18 |
| TGA7 | 25 | 15 |
| TGA8 | 16 | 15 |
| TGA9 | 10 | 8 |
| TGA10 | 15 | 11 |
| TGA11 | 25 | 17 |
| | 19.4 ± 1.79 | 14.4 ± 1.14 |
| Therapy Group B | | |
| TGB1 | 21 | 19 |
| TGB2 | 17 | 14 |
| TGB3 | 23 | 14 |
| TGB4 | 24 | 12 |
| TGB5 | 19 | 19 |
| TGB6 | 16 | — |
| TGB7 | 24 | 13 |
| TGB8 | 19 | 14 |
| | 20.4 ± 1.24 | 15.0 ± 1.17 |
| Therapy Group C | | |
| TGC1 | 15 | 9 |
| TGC2 | 21 | 21 |
| TGC3 | 18 | 13 |
| TGC4 | 16 | 16 |
| TGC5 | 19 | 9 |
| TGC6 | 21 | 21 |
| TGC7 | 17 | 17 |
| TGC8 | 20 | 13 |
| TGC9 | 20 | 20 |
| | 18.6 ± 0.81 | 15.4 ± 1.75 |

TABLE 29

| Patient code | Abzyme activity Day 0 | Abzyme activity Day 60 | Rose Blackthorn Score Day 0 | Rose Blackthorn Score Day 60 |
|---|---|---|---|---|
| TGA2 | 90 | 3.3 | 22 | 19 |
| TGA3 | 80 | 6.7 | 12 | 10 |
| TGA4 | 40 | 0 | 19 | 13 |

TABLE 29-continued

| Patient code | Abzyme activity Day 0 | Abzyme activity Day 60 | Rose Blackthorn Score Day 0 | Rose Blackthorn Score Day 60 |
|---|---|---|---|---|
| TGA6 | 15 | 6.7 | 21 | 18 |
| TGB3 | 15 | 0 | 23 | 14 |
| TGC5 | 45 | 0 | 19 | 9 |
| TGC7 | 140 | 20 | 17 | 17 |

TABLE 30

| Compound and its concentration | Lipid oxidising activity of anti-Chlamydia abzymes in, µM MDA/ml* | Comments |
|---|---|---|
| Control Azithromycin** Suspension in water | 61 | Antioxidant properties are comparable with or stronger than α-Tocopherol |
| 20 µM | 0 | |
| 10 µM | 0 | |
| 2 µM | 0 | |
| 1 µM | 19 | |
| Suspension in DMSO | | |
| 5 µM | 0 | |
| 1 µM | 7 | |
| α-Tocopherol in DMSO | | |
| 10 µM | 0 | |
| 1 µM | 15 | |

TABLE 31

| DRUGS | Anti-Abzyme activity, in µM MDA/ml |
|---|---|
| Control | 21.7 |
| Beta Blocker | |
| 1. Propranolol Hydrochloride OBSIDAN | |
| 175 µM | 21.3 |
| 35 µM | 18.3 |
| Nitrates | |
| 1. Glyceryl Trinitrate PERLINGANIT | |
| 220 µM | 0 |
| 44 µM | 0 |
| 22 µM | 0 |
| 4.4 µM | 0 |

TABLE 31-continued

| DRUGS | Anti-Abzyme activity, in μM MDA/ml |
|---|---|
| 2. Isosorbide Dinitrate ISOKET | |
| 211 μM | 0 |
| 42 μM | 0 |
| Magnesium | |
| 1. Magnesium Sulfate | |
| 101 μM | 0 |
| 51 μM | 0 |
| 40 μM | 16 |
| 20 μM | 26 |
| Heparin | |
| 1 Heparin | |
| 0.1 mg/ml | 19.7 |
| 2. Nadroparin Calcium FRAXIPARINE | |
| 465 UI | 12.8 |
| 95 UI | 20.5 |
| Calcium-Channel Blocker | |
| 1. Verapamil Hydrochloride ISOPTIN | |
| 51 μM | 3 |
| 10.2 μM | 24.0 |
| 5.1 μM | 21.5 |
| Corticosteroids | |
| 1. Dexamethasone | |
| 25 μM | 24.5 |
| 12.5 μM | 20.1 |
| Antibiotics | |
| 1. Lincomycin Hydrochloride | |
| 13 μM | 30.3 |
| 6.5 μM | 28.5 |

TABLE 32

| | | Abbreviation for clotting time measurements | Means of results from patient therapy groups A, B, C and D groups | Abbreviation for clotting time measurements | Not treated Patient Control Group (PCG) | Our Clinically Healthy Control Group |
|---|---|---|---|---|---|---|
| Coagulation* | Before treatment | APTT | 22.4 ± 0.69 | | | |
| | | PT | 13.5 ± 0.94 | | | |
| | | SCT | 151 ± 15.0 | APTT | 25.2 ± 1.37 | 49.1 ± 7.00 |
| | | KCT | 51.2 ± 4.59 | | | |
| | 60 days after treatment | APTT | 46.9 ± 6.45 p < 0.005* | PT | 17.3 ± 4.05 | 23.7 ± 4.01 |
| | | PT | 25.3 ± 4.05 p < 0.05* | SCT | 137 ± 11.5 | 248 ± 10.0 |
| | | SCT | 235 ± 17.9 p < 0.005* | KCT | 50.3 ± 2.16 | 133 ± 23.7 |
| | | KCT | 126 ± 34.2 p > 0.05 | | | |

The invention claimed is:

1. A method of determining the efficacy of treating an individual having an atherosclerotic disorder comprising administering to said individual one or both compounds selected from the group consisting of azithromycin and aspirin, the method further comprising:

(i) providing a serum sample from said individual following said administration, and (ii) determining the presence or absence of lipid oxidizing IgG molecules which bind to a Chlamydia cell, wherein the absence of lipid oxidising IgG molecules which bind to a Chlamydia cell in said sample is indicative that said atherosclerotic disorder is treated by said administration.

2. The method of 1 further comprising determining the lipid oxidation activity of said IgG molecules from a sample obtained from the individual prior to said administration.

3. A method of determining the efficacy of treating an individual having an atherosclerotic disorder comprising;

administering to said individual one or both compounds selected from the group consisting of azithromvcin and aspirin, the method further comprising;

(i) providing a serum sample from said individual following said administration, (ii) contacting the same with a Chlamydia cell and determining lipid oxidation in said sample and (iii) comparing the lipid oxidation in the sample in the presence and absence of said Chlamydia cell, wherein the absence of an increase in lipid oxidation in the presence of the Chlamydia cell in said sample is indicative that said atherosclerotic disorder is treated by said administration.

* * * * *